(12) United States Patent
Schuckmann et al.

(10) Patent No.: US 9,999,423 B2
(45) Date of Patent: Jun. 19, 2018

(54) TRANSLATABLE ARTICULATION JOINT UNLOCKING FEATURE FOR SURGICAL STAPLER

(71) Applicant: Ethicon Endo-Surgery, Inc., Cincinnati, OH (US)

(72) Inventors: John C. Schuckmann, Cincinnati, OH (US); David Bruns, Kettering, OH (US)

(73) Assignee: Ethicon LLC, Guaynabo, PR (US)

( * ) Notice: Subject to any disclaimer, the term of this patent is extended or adjusted under 35 U.S.C. 154(b) by 650 days.

(21) Appl. No.: 14/314,722

(22) Filed: Jun. 25, 2014

(65) Prior Publication Data

US 2015/0374365 A1 Dec. 31, 2015

(51) Int. Cl.
| | |
|---|---|
| *A61B 17/04* | (2006.01) |
| *A61B 17/10* | (2006.01) |
| *A61B 17/068* | (2006.01) |
| *A61B 17/072* | (2006.01) |
| *A61B 17/29* | (2006.01) |

(52) U.S. Cl.
CPC ...... *A61B 17/068* (2013.01); *A61B 17/07207* (2013.01); *A61B 2017/2923* (2013.01); *A61B 2017/2927* (2013.01); *A61B 2017/2946* (2013.01)

(58) Field of Classification Search
CPC .... A61B 2017/2905; A61B 2017/2927; A61B 2017/320052
See application file for complete search history.

(56) References Cited

U.S. PATENT DOCUMENTS

| | | | |
|---|---|---|---|
| 4,805,823 | A | 2/1989 | Rothfuss |
| 5,415,334 | A | 5/1995 | Williamson, IV et al. |

(Continued)

FOREIGN PATENT DOCUMENTS

| | | | |
|---|---|---|---|
| EP | 1 709 913 A2 | 10/2006 | |
| EP | 1 915 953 A1 | 4/2008 | |

(Continued)

OTHER PUBLICATIONS

U.S. Appl. No. 13/780,067, filed Feb. 28, 2013.
(Continued)

*Primary Examiner* — Hemant M Desai
*Assistant Examiner* — Eyamindae Jallow
(74) *Attorney, Agent, or Firm* — Frost Brown Todd LLC

(57) ABSTRACT

An apparatus comprises a body, a shaft assembly, an end effector, and an articulation joint. The end effector is operable to manipulate (e.g., staple) tissue. The articulation joint couples the end effector with the shaft assembly and permits the end effector to deflect away from the longitudinal axis of the shaft assembly. The articulation joint comprises a locking assembly, which is operable to selectively lock the angular position of the end effector relative to the longitudinal axis. The locking assembly comprises a first locking member and a second locking member. The first locking member is unitarily secured to the end effector. The second locking member is movable along a first axis to selectively engage the first locking member to thereby selectively lock the angular position of the end effector relative to the longitudinal axis of the shaft assembly. The first axis is perpendicular to the longitudinal axis.

18 Claims, 36 Drawing Sheets

(56) References Cited

U.S. PATENT DOCUMENTS

| | | |
|---|---|---|
| 5,465,895 A | 11/1995 | Knodel et al. |
| 5,597,107 A | 1/1997 | Knodel et al. |
| 5,632,432 A | 5/1997 | Schulze et al. |
| 5,673,840 A | 10/1997 | Schulze et al. |
| 5,673,841 A | 10/1997 | Schulze et al. |
| 5,704,534 A | 1/1998 | Huitema et al. |
| 5,792,135 A | 8/1998 | Madhani et al. |
| 5,814,055 A | 9/1998 | Knodel et al. |
| 5,817,084 A | 10/1998 | Jensen |
| 5,823,066 A * | 10/1998 | Huitema .......... A61B 17/07207 227/175.1 |
| 5,878,193 A | 3/1999 | Wang et al. |
| 6,231,565 B1 | 5/2001 | Tovey et al. |
| 6,364,888 B1 | 4/2002 | Niemeyer et al. |
| 6,783,524 B2 | 8/2004 | Anderson et al. |
| 6,848,344 B2 | 2/2005 | Rocco |
| 6,978,921 B2 | 12/2005 | Shelton, IV et al. |
| 7,000,818 B2 | 2/2006 | Shelton, IV et al. |
| 7,143,923 B2 | 12/2006 | Shelton, IV et al. |
| 7,303,108 B2 | 12/2007 | Shelton, IV |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,524,320 B2 | 4/2009 | Tierney et al. |
| 7,556,185 B2 * | 7/2009 | Viola .............. A61B 17/07207 227/175.1 |
| 7,644,848 B2 | 1/2010 | Swayze et al. |
| 7,691,098 B2 | 4/2010 | Wallace et al. |
| 7,721,930 B2 | 5/2010 | McKenna et al. |
| 7,806,891 B2 | 10/2010 | Nowlin et al. |
| 8,210,411 B2 | 7/2012 | Yates et al. |
| 8,408,439 B2 | 4/2013 | Huang et al. |
| 8,453,914 B2 | 6/2013 | Laurent et al. |
| 8,479,969 B2 | 7/2013 | Shelton, IV et al. |
| 8,573,461 B2 | 11/2013 | Shelton, IV et al. |
| 8,573,465 B2 | 11/2013 | Shelton, IV |
| 8,602,288 B2 | 12/2013 | Shelton, IV et al. |
| 8,616,431 B2 | 12/2013 | Timm et al. |
| 8,783,541 B2 | 7/2014 | Shelton, IV et al. |
| 8,800,838 B2 | 8/2014 | Shelton, IV et al. |
| 2012/0199630 A1 | 8/2012 | Shelton, IV et al. |
| 2012/0199632 A1 | 8/2012 | Spivey et al. |
| 2013/0012957 A1 | 1/2013 | Shelton, IV et al. |

FOREIGN PATENT DOCUMENTS

| | | |
|---|---|---|
| JP | 2013-208476 A | 10/2013 |
| WO | WO 2004/112618 A2 | 10/2006 |

OTHER PUBLICATIONS

U.S. Appl. No. 13/780,082, filed Feb. 28, 2013.
U.S. Appl. No. 13/780,106, filed Feb. 28, 2013.
U.S. Appl. No. 13/780,120, filed Feb. 28, 2013.
U.S. Appl. No. 13/780,162, filed Feb. 28, 2013.
U.S. Appl. No. 13/780,171, filed Feb. 28, 2013.
U.S. Appl. No. 13/780,379, filed Feb. 28, 2013.
U.S. Appl. No. 13/780,402, filed Feb. 28, 2013.
U.S. Appl. No. 13/780,417, filed Feb. 28, 2013.
U.S. Appl. No. 14/314,108, filed Jun. 25, 2014.
U.S. Appl. No. 14/314,125, filed Jun. 25, 2014.
U.S. Appl. No. 14/314,164, filed Jun. 25, 2014.
U.S. Appl. No. 14/314,276, filed Jun. 25, 2014.
U.S. Appl. No. 14/314,626, filed Jun. 25, 2014.
European Search Report and Written Opinion, extended, dated Sep. 16, 2015 for Application No. EP 15173533.9, 9 pgs.
European Exam Report dated Mar. 28, 2017 for Application No. EP 15173533.9, 4 pgs.
International Search Report and Written Opinion dated Oct. 6, 2015 for Application No. PCT/US2015/034617, 12 pgs.

* cited by examiner

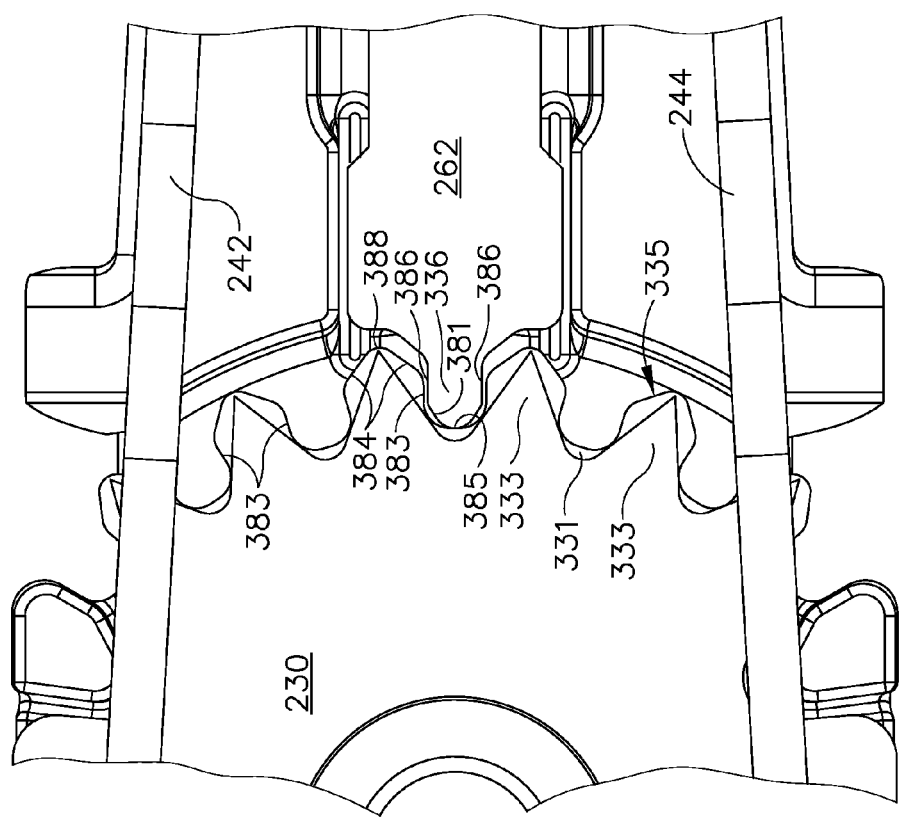

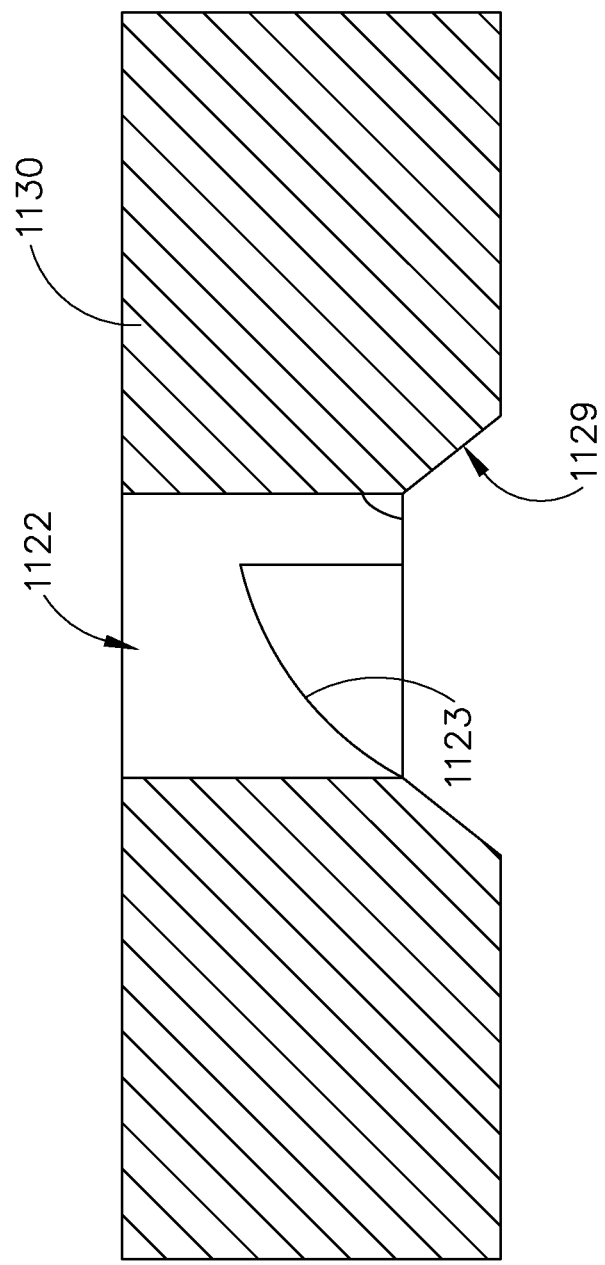

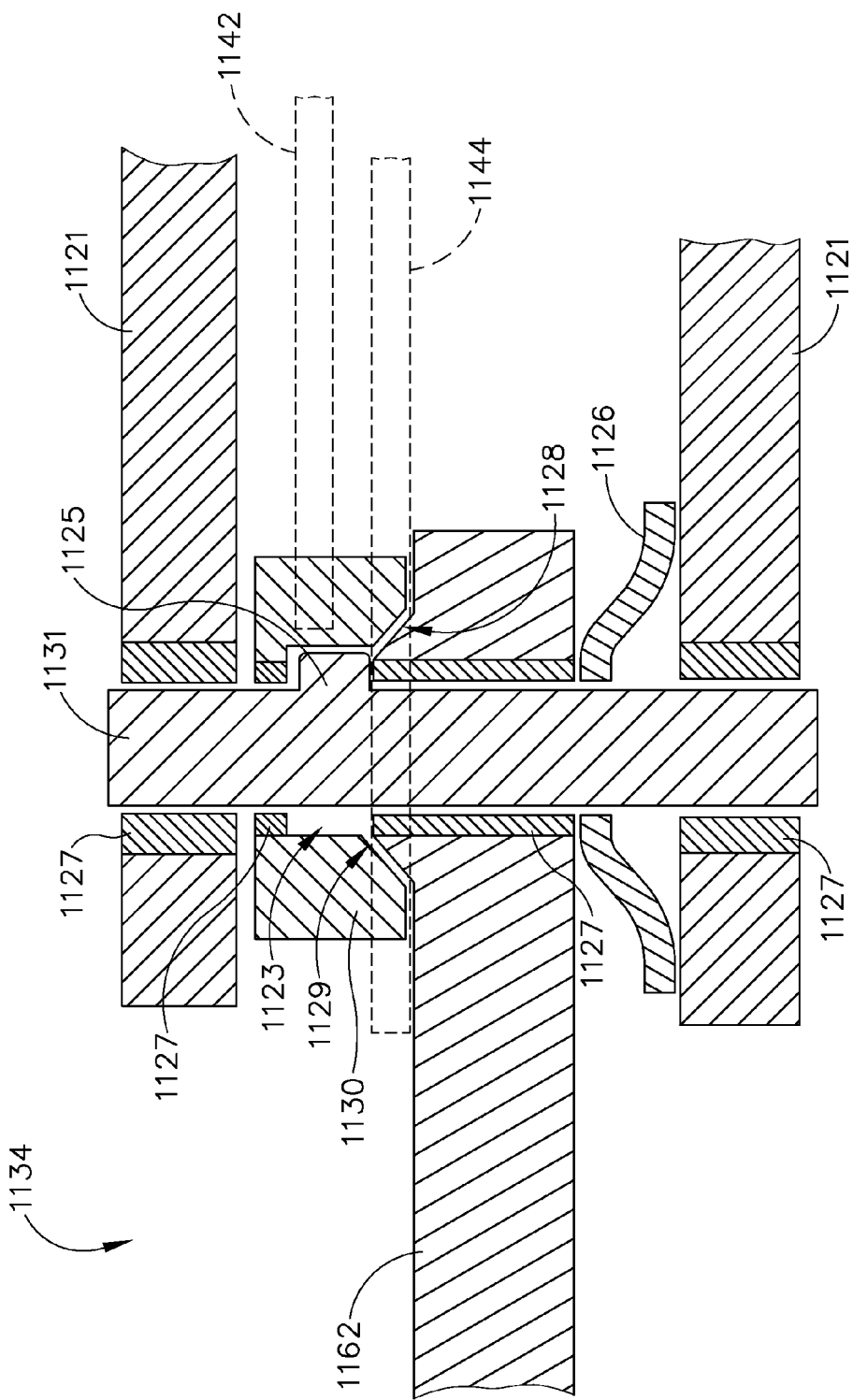

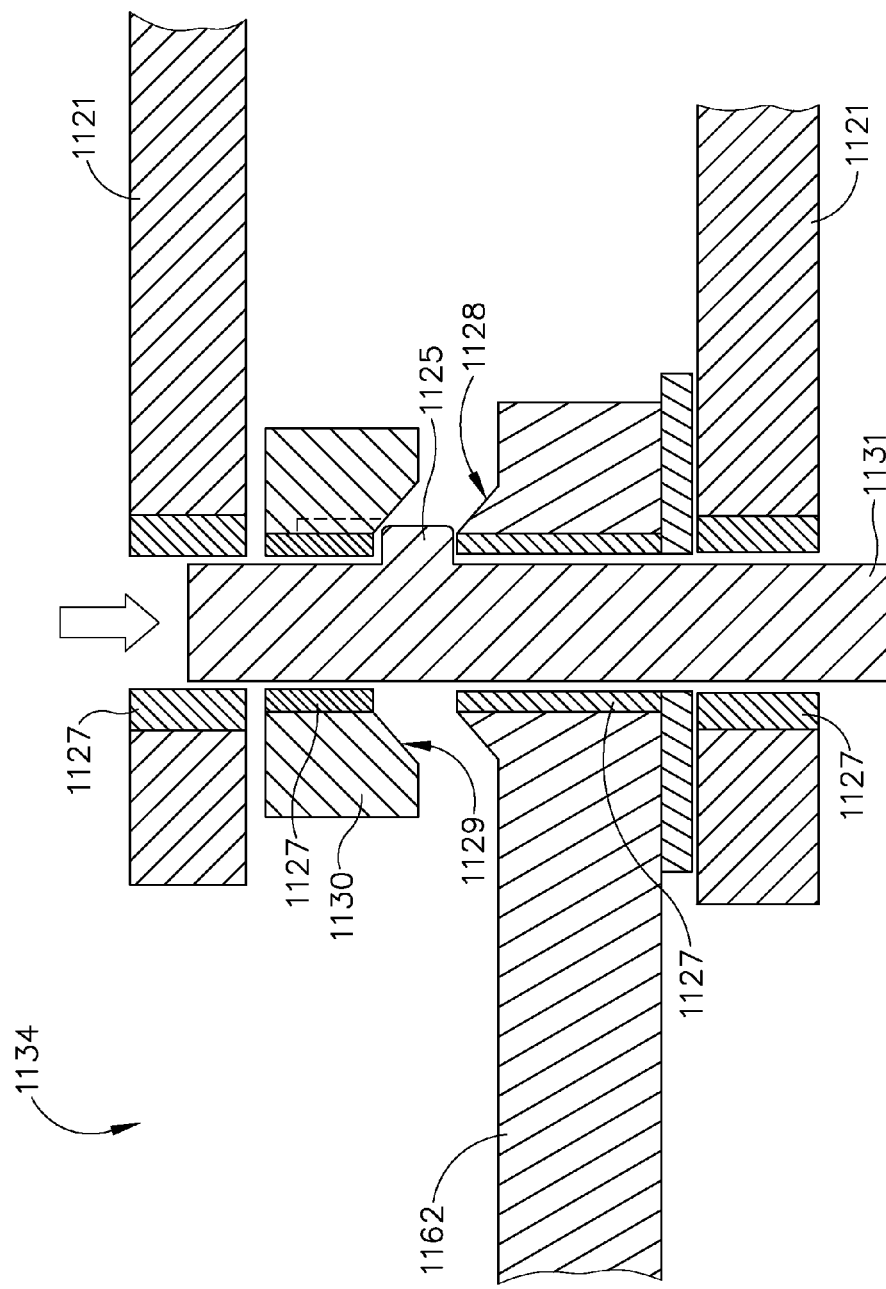

TRANSLATABLE ARTICULATION JOINT UNLOCKING FEATURE FOR SURGICAL STAPLER

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Pub. No. 2014/0243801, entitled "Surgical Instrument End Effector Articulation Drive with Pinion and Opposing Racks," published Aug. 28, 2014, now U.S. Pat. No. 9,186, 142, issued Nov. 17, 2015; U.S. Pub. No. 2014/0239041, entitled "Lockout Feature for Movable Cutting Member of Surgical Instrument," published Aug. 28, 2014, now U.S. Pat. No. 9,717,497, issued Aug. 1, 2017; U.S. Pub. No. 2014/0239042, entitled "Integrated Tissue Positioning and Jaw Alignment Features for Surgical Stapler," published Aug. 28, 2014, now U.S. Pat. No. 9,517,065, issued Dec. 13, 2016; U.S. Pub. No. 2014/0239036, entitled "Jaw Closure Feature for End Effector of Surgical Instrument," published Aug. 28, 2014, now U.S. Pat. No. 9,839,421, issued Dec. 12, 2017; U.S. Pub. No. 2014/0239040, entitled "Surgical Instrument with Articulation Lock having a Detenting Binary Spring," now U.S. Pat. No. 9,867,615, issued Jan. 16, 2018; U.S. Pub. No. 2014/0239043, entitled "Distal Tip Features for End Effector of Surgical Instrument," published Aug. 28, 2014, now U.S. Pat. No. 9,622,746, issued Apr. 18, 2017; U.S. Pub. No. 2014/0239037, entitled "Staple Forming Features for Surgical Stapling Instrument," published Aug. 28, 2014; U.S. Pub. No. 2014/0239038, entitled "Surgical Instrument with Multi-Diameter Shaft," published Aug. 28, 2014, now U.S. Pat. No. 9,795,379, issued Oct. 24, 2017; and U.S. Pub. No. 2014/0239044, entitled "Installation Features for Surgical Instrument End Effector Cartridge," published Aug. 28, 2014, now U.S. Pat. No. 9,808, 248, issued Nov. 7, 2017. The disclosure of each of the above-cited U.S. Patent Applications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 19 depicts a top plan, enlarged view of the interface of the cam members and the lock bar of the shaft assembly of FIG. 13A;

FIG. 24 depicts a side, cross-sectional view of a helical cam of the cam assembly depicted in FIG. 23, taken along line 24-24 of FIG. 23;

FIG. 25A depicts a side, cross-sectional view of an exemplary alternative articulation joint utilizing the cam assembly of FIG. 23;

FIG. 25B depicts a side, cross-sectional view of the articulation joint of FIG. 25A in an unlocked position;

Figure 1:
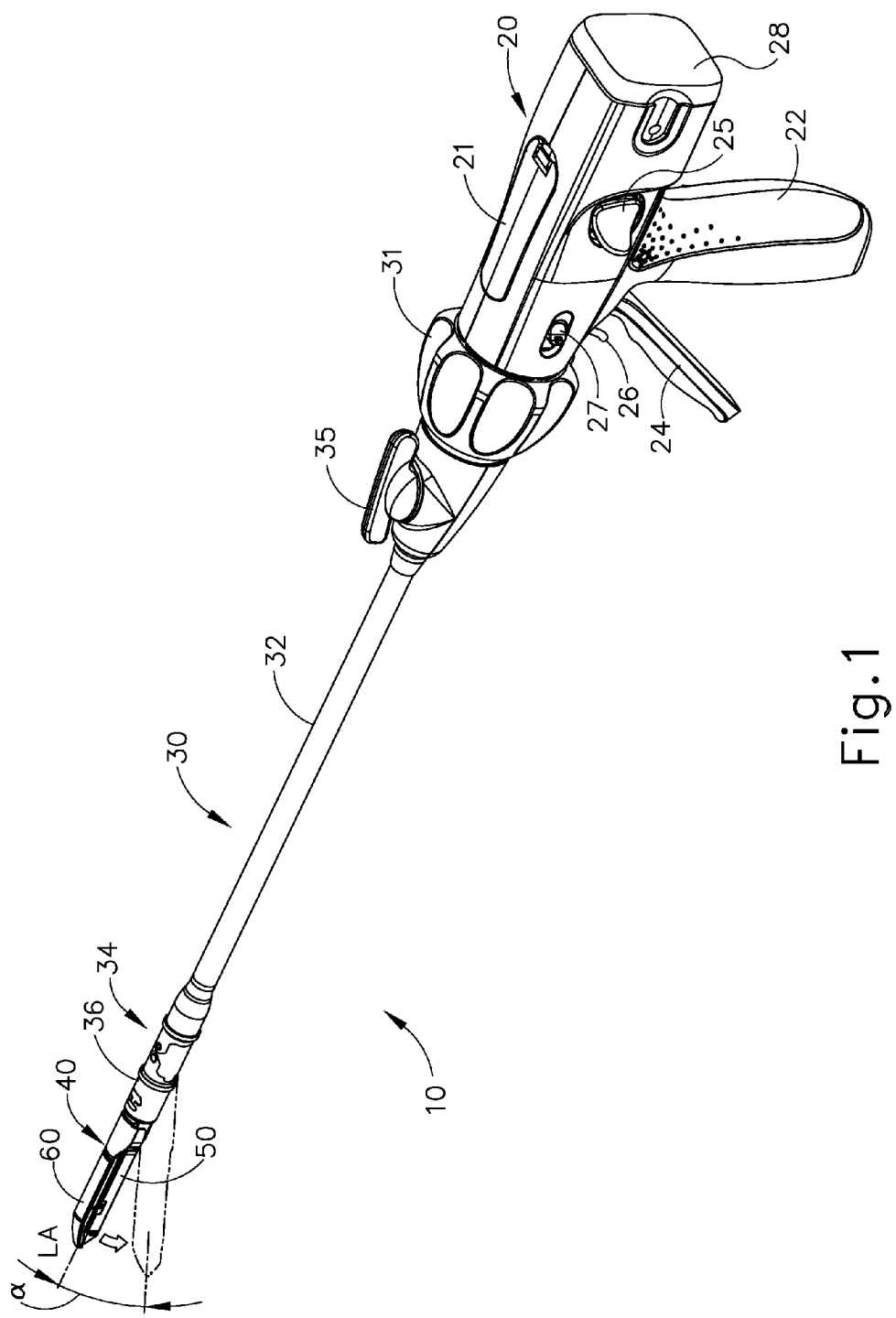
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

Figure 2:
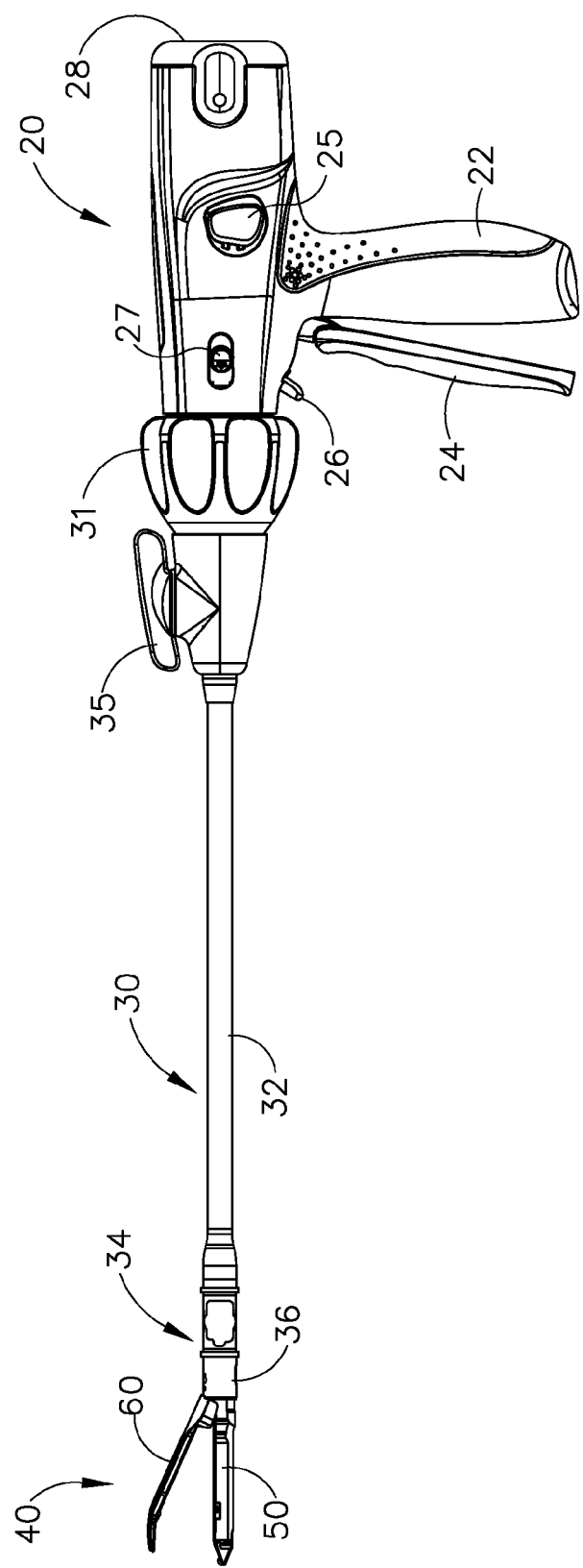
FIG. 2 depicts a side elevational view of the instrument of FIG. 1.

As shown in FIGS. 1-2, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes an anvil release button (25), a firing beam reverse switch (27), and a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 3:
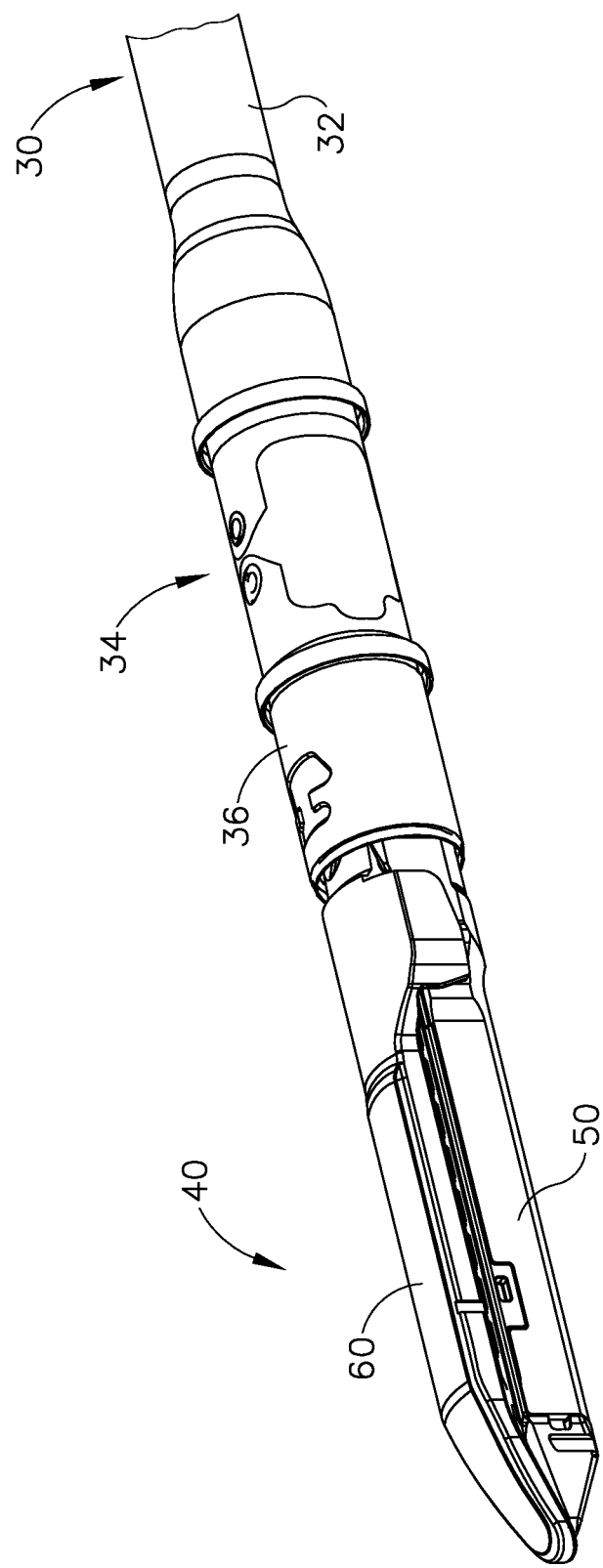
FIG. 3 depicts a perspective view of an end effector of the instrument of FIG. 1, with the end effector in a closed configuration.

As shown in FIGS. 1-3, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (a). End effector (40) may thereby reach behind an organ or approach tissue from a desired angle or for other reasons. In some versions, articulation section (34) enables deflection of end effector (40) along a single plane. In some other versions, articulation section (34) enables deflection of end effector along more than one plane. In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). By way of example only, rotation of knob (35) clockwise may cause corresponding clockwise pivoting of closure ring (36) and end effector (40) at articulation section (34). Articulation section (34) is configured to communicate longitudinal translation of closure tube (32) to closure ring (36), regardless of whether articulation section (34) is in a straight configuration or an articulated configuration.

In some versions, articulation section (34) and/or articulation control knob (35) are/is constructed and operable in accordance with at least some of the teachings of U.S. Pub. No. 2014/0243801, entitled "Surgical Instrument End Effector Articulation Drive with Pinion and Opposing Racks," published Aug. 28, 2014, now U.S. Pat. No. 9,186,142, issued Nov. 17, 2015, the disclosure of which is incorporated by reference herein. Articulation section (34) may also be constructed and operable in accordance with at least some of the teachings of U.S. Pub. No. 2015/0374390, entitled "Articulation Drive Features for Surgical Stapler," published Dec. 31, 2015, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). In some versions, rotation knob (31) is operable to selectively lock the angular position of shaft assembly (30) and end effector (40) relative to handle assembly (20) about the longitudinal axis (LA) of shaft assembly (30). For instance, rotation knob (31) may be translatable between a first longitudinal position, in which shaft assembly (30) and end effector (40) are rotatable relative to handle assembly (20) about the longitudinal axis (LA) of shaft assembly (30); and a second longitudinal position, in which shaft assembly (30) and end effector (40) are not rotatable relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, now U.S. Pat. No. 9,795,379, issued Oct. 24, 2017, the disclosure of which is incorporated by reference herein. Other suitable configurations for shaft assembly (30) will be apparent to those of ordinary skill in the art in view of the teachings herein.

B. Exemplary End Effector

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Pins (66) and slots (54) are shown in FIG. 5. Anvil (60) is pivotable toward and away from lower jaw (50) between an open position (shown in FIGS. 2 and 4) and a closed position (shown in FIGS. 1, 3, and 7A-7B). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 5, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, now U.S. Pat. No. 9,808,248, issued Nov. 7, 2017, the disclosure of which is incorporated by reference herein. Other suitable forms that lower jaw (50) may take will be apparent to those of ordinary skill in the art in view of the teachings herein.

Figure 4:
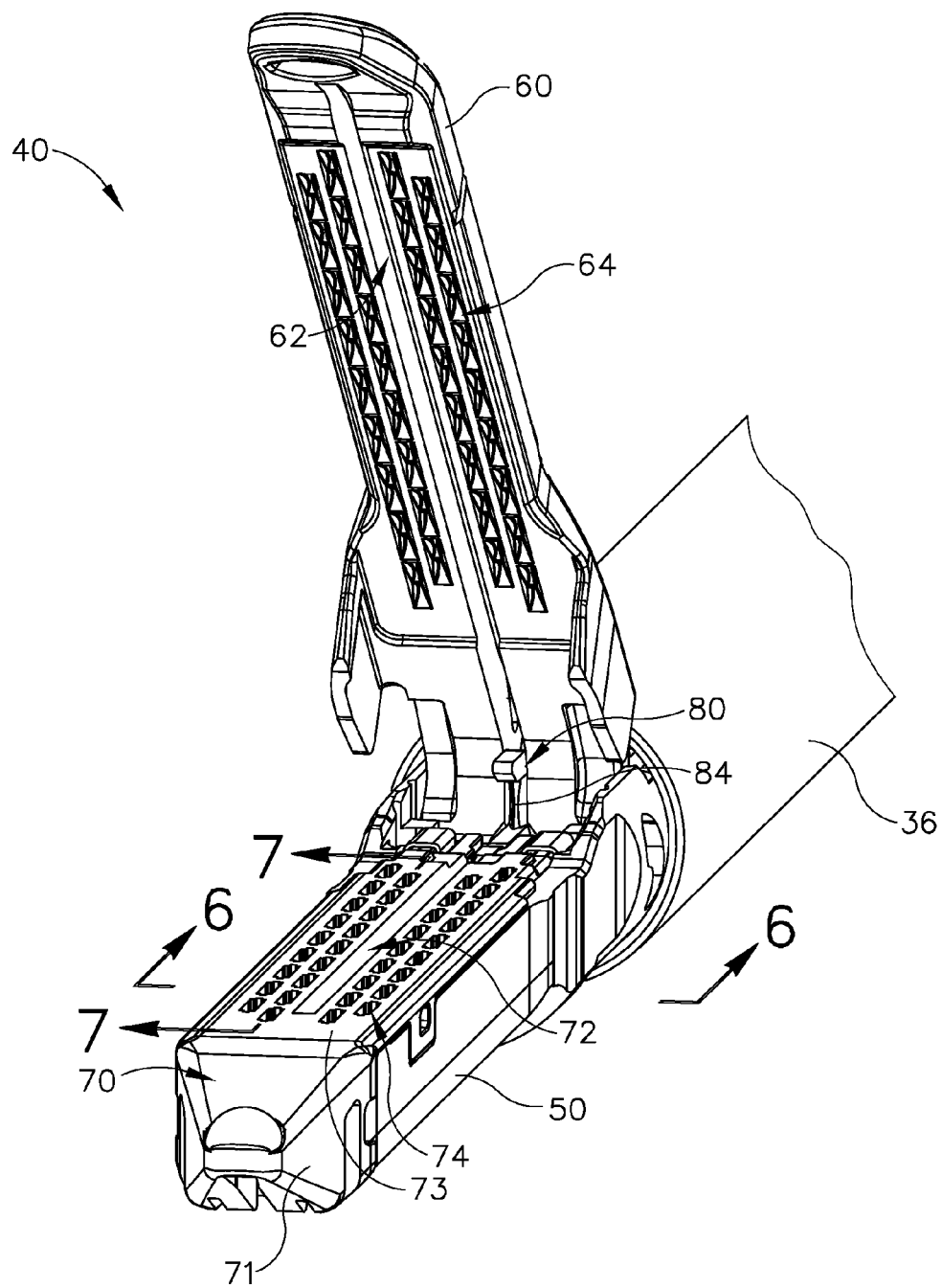
FIG. 4 depicts a perspective view of the end effector of FIG. 3, with the end effector in an open configuration.
Figure 5:
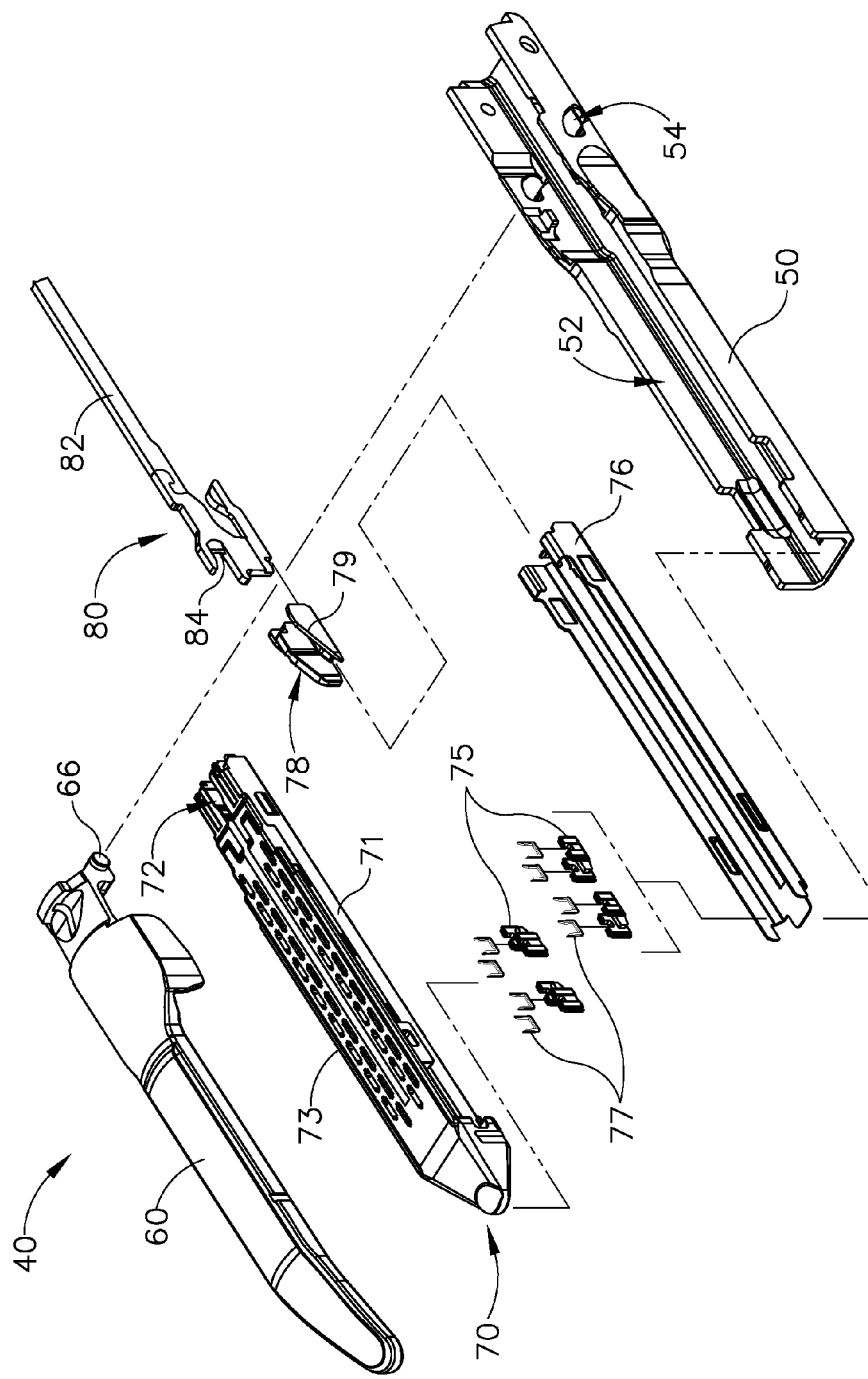
FIG. 5 depicts an exploded perspective view of the end effector of FIG. 3.
Figure 6:
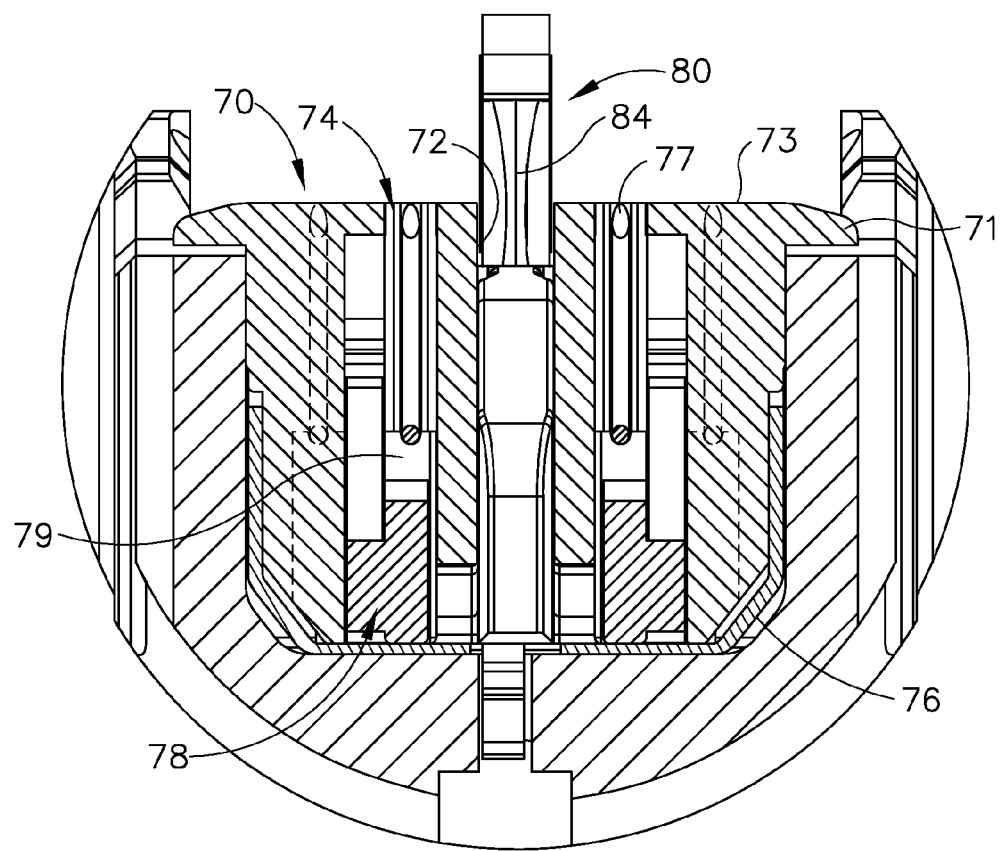
FIG. 6 depicts a cross-sectional end view of the end effector of FIG. 3, taken along line 6-6 of FIG. 4.
Figure 7A:
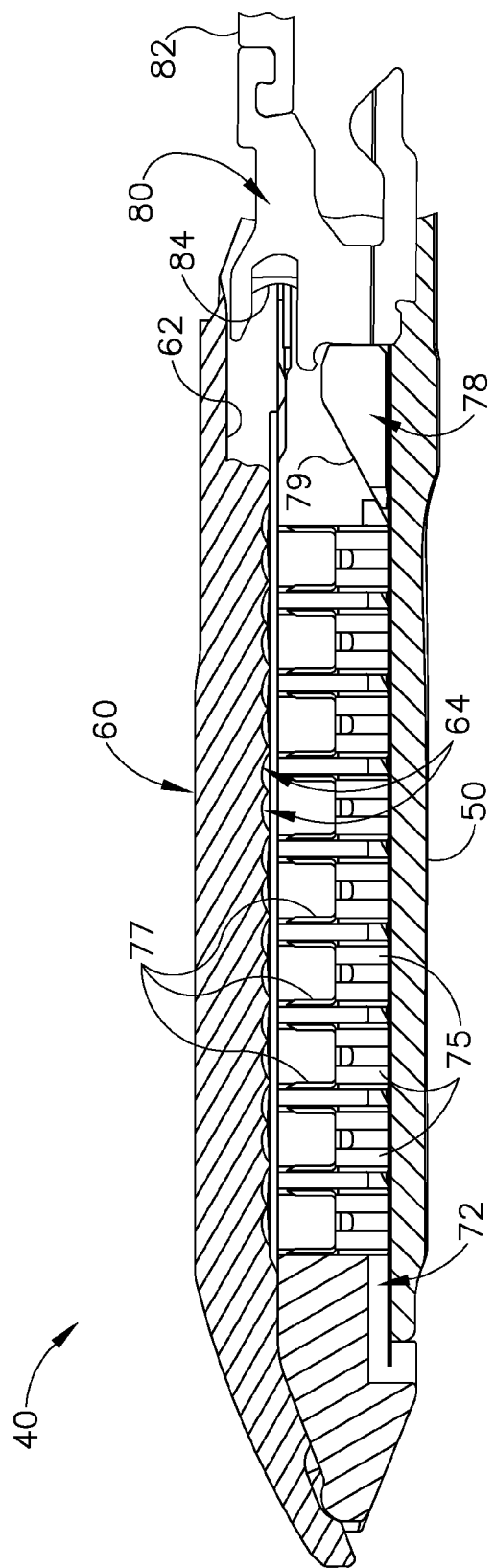
FIG. 7A depicts a cross-sectional side view of the end effector of FIG. 3, taken along line 7-7 of FIG. 4, with the firing beam in a proximal position.

As best seen in FIGS. 4-6, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). As will be described in greater detail below, staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position as shown in FIG. 7A, staple drivers (75) are in downward positions and staples (77) are located in staple pockets (74). As wedge sled (78) is driven to the distal position shown in FIG. 7B by a translating knife member (80), wedge sled (78) drives staple drivers (75) upwardly, thereby driving staples (77) out of staple pockets (74) and into staple forming pockets (64). Thus, staple drivers (75) translate along a vertical dimension as wedge sled (78) translates along a horizontal dimension.

It should be understood that the configuration of staple cartridge (70) may be varied in numerous ways. For instance, staple cartridge (70) of the present example includes two longitudinally extending rows of staple pockets (74) on one side of channel (72); and another set of two longitudinally extending rows of staple pockets (74) on the other side of channel (72). However, in some other versions, staple cartridge (70) includes three, one, or some other number of staple pockets (74) on each side of channel (72). In some versions, staple cartridge (70) is constructed and operable in accordance with at least some of the teachings of U.S. Pub. No. 2014/0239042, entitled "Integrated Tissue Positioning and Jaw Alignment Features for Surgical Stapler," published Aug. 28, 2014, now U.S. Pat. No. 9,517,065, issued Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, now U.S. Pat. No. 9,808,248, issued Nov. 7, 2017, the disclosure of which is incorporated by reference herein. Other suitable forms that staple cartridge (70) may take will be apparent to those of ordinary skill in the art in view of the teachings herein.

As best seen in FIG. 4, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). In particular, staple forming pockets (64) are configured to bend the legs of staples (77) to secure the formed staples (77) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, now U.S. Pat. No. 9,517,065, issued Dec. 13, 2016, at least some of the teachings of U.S. Pub. No. 2014/0239036, entitled "Jaw Closure Feature for End Effector of Surgical Instrument," published Aug. 28, 2014, now U.S. Pat. No. 9,839,421, issued Dec. 12, 2017; and/or at least some of the teachings of U.S. Pub. No. 2014/0239037, entitled "Staple Forming Features for Surgical Stapling Instrument," published Aug. 28, 2014, the disclosure of which is incorporated by reference herein. Other suitable forms that anvil (60) may take will be apparent to those of ordinary skill in the art in view of the teachings herein.

Figure 7B:
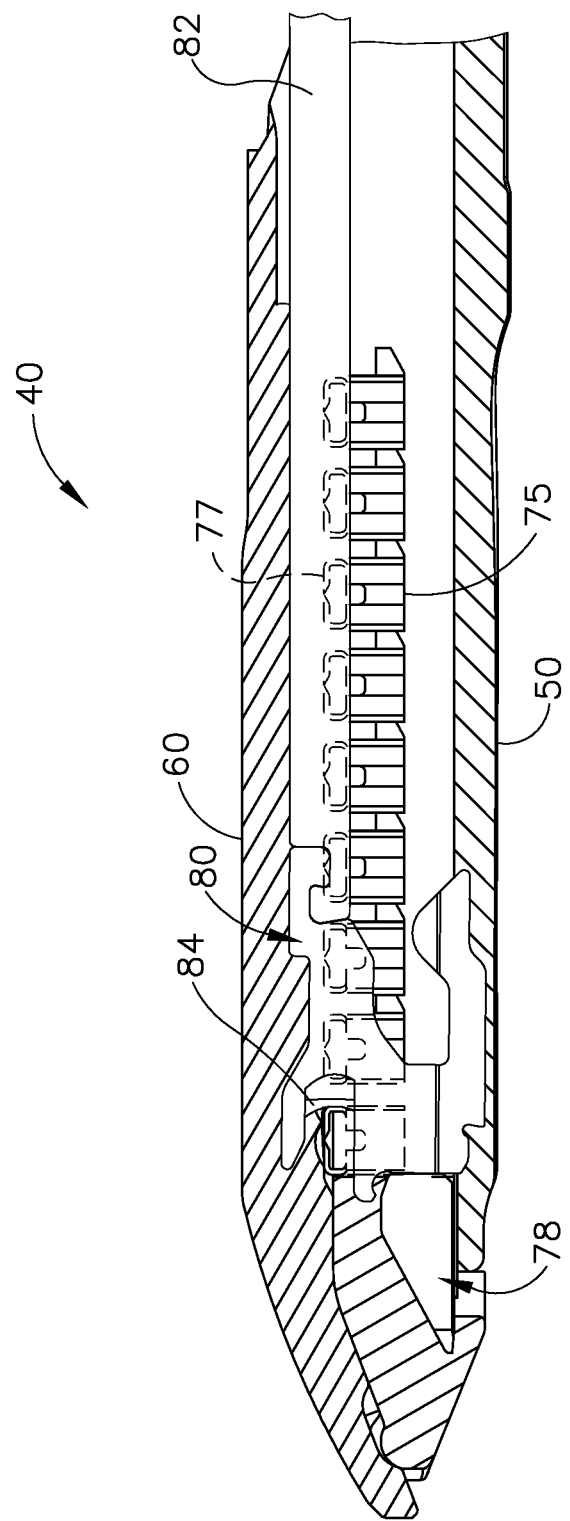
FIG. 7B depicts a cross-sectional side view of the end effector of FIG. 3, taken along line 7-7 of FIG. 4, with the firing beam in a distal position.

In the present example, a knife member (80) is configured to translate through end effector (40). As best seen in FIGS. 5 and 7A-7B, knife member (80) is secured to the distal end of a firing beam (82), which extends through a portion of shaft assembly (30). As best seen in FIGS. 4 and 6, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above and as shown in FIGS. 7A-7B, knife member (80) also drives wedge sled (78) distally as knife member (80) translates distally through end effector (40), thereby driving staples (77) through tissue and against anvil (60) into formation. Various features that may be used to drive knife member (80) distally through end effector (40) will be described in greater detail below.

In some versions, end effector (40) includes lockout features that are configured to prevent knife member (80) from advancing distally through end effector (40) when a staple cartridge (70) is not inserted in lower jaw (50). In addition or in the alternative, end effector (40) may include lockout features that are configured to prevent knife member (80) from advancing distally through end effector (40) when a staple cartridge (70) that has already been actuated once (e.g., with all staples (77) deployed therefrom) is inserted in lower jaw (50). By way of example only, such lockout features may be configured in accordance with at least some of the teachings of U.S. Pub. No. 2014/0239041, entitled "Lockout Feature for Movable Cutting Member of Surgical Instrument," published Aug. 28, 2014, now U.S. Pat. No. 9,717,497, issued Aug. 1, 2017, the disclosure of which is incorporated by reference herein; and/or at least some of the teachings of U.S. Pub. No. 2015/0374373, entitled "Method of Using Lockout Features for Surgical Stapler Cartridge," published Dec. 31, 2015, the disclosure of which is incorporated by reference herein. Other suitable forms that lockout features may take will be apparent to those of ordinary skill in the art in view of the teachings herein. Alternatively, end effector (40) may simply omit such lockout features.

C. Exemplary Actuation of Anvil

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, now U.S. Pat. No. 9,839,421, issued Dec. 12, 2017, the disclosure of which is incorporated by reference herein; and/or in accordance with at least some of the teachings of U.S. Pub. No. 2015/0374361, entitled "Jaw Opening Feature for Surgical Stapler," published Dec. 31, 2015, the disclosure of which is incorporated by reference herein. Exemplary features that may be used to provide longitudinal translation of closure ring (36) relative to end effector (40) will be described in greater detail below.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of trigger (24) and closure tube (32), thereby locking anvil (60) in a fully closed position relative to lower jaw (50). These locking features are released by actuation of anvil release button (25). Anvil release button (25) is configured and positioned to be actuated by the thumb of the operator hand that grasps pistol grip (22). In other words, the operator may grasp pistol grip (22) with one hand, actuate closure trigger (24) with one or more fingers of the same hand, and then actuate anvil release button (25) with the thumb of the same hand, without ever needing to release the grasp of pistol grip (22) with the same hand. Other suitable features that may be used to actuate anvil (60) will be apparent to those of ordinary skill in the art in view of the teachings herein.

D. Exemplary Actuation of Firing Beam

Figure 9:
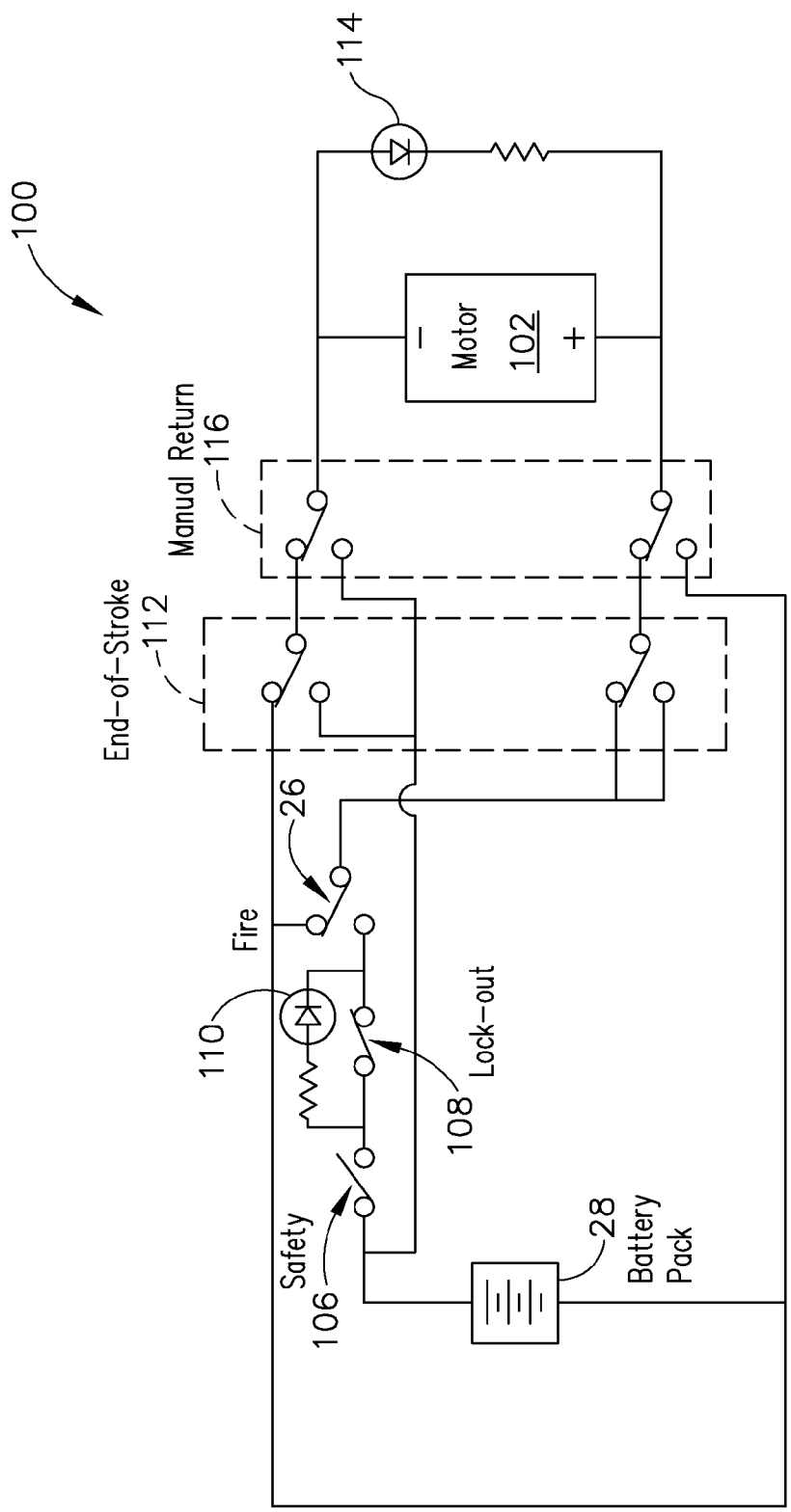
FIG. 9 depicts a schematic view of an exemplary control circuit for use in the instrument of FIG. 1.

In the present example, instrument (10) provides motorized control of firing beam (82). FIGS. 9-12 show exemplary components that may be used to provide motorized control of firing beam (82). In particular, FIG. 9 shows an exemplary control circuit (100) that may be used to power an electric motor (102) with electric power from a battery pack (28) (also shown in FIGS. 1-2). Electric motor (102) is operable to translate firing beam (82) longitudinally as will be described in greater detail below. It should be understood that the entire control circuit (100), including motor (102) and battery pack (28), may be housed within handle assembly (20). FIG. 9 shows firing trigger (26) as an open switch, though it should be understood that this switch is closed when firing trigger (26) is actuated. Circuit (100) of this example also includes a safety switch (106) that must be closed in order to complete circuit (100), though it should be understood that safety switch (106) is merely optional. Safety switch (106) may be closed by actuating a separate button, slider, or other feature on handle assembly (20). Safety switch (106) may also provide a mechanical lockout of firing trigger (26), such that firing trigger (26) is mechanically blocked from actuation until safety switch (106) is actuated.

Circuit (100) of the present example also includes a lockout switch (108), which is configured to be closed by default but is automatically opened in response to a lockout condition. By way of example only, a lockout condition may include one or more of the following: the absence of a cartridge (70) in lower jaw (50), the presence of a spent (e.g., previously fired) cartridge (70) in lower jaw (50), an insufficiently closed anvil (60), a determination that instrument (10) has been fired too many times, and/or any other suitable conditions. Various sensors, algorithms, and other features that may be used to detect lockout conditions will be apparent to those of ordinary skill in the art in view of the teachings herein. Similarly, other suitable kinds of lockout conditions will be apparent to those of ordinary skill in the art in view of the teachings herein. It should be understood that circuit (100) is opened and thus motor (102) is inoperable when lockout switch (108) is opened. A lockout indicator (110) (e.g., an LED, etc.) is operable to provide a visual indication of the status of lockout switch (108). By way of example only, lockout switch (108), lockout indicator (110), and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Figure 12:
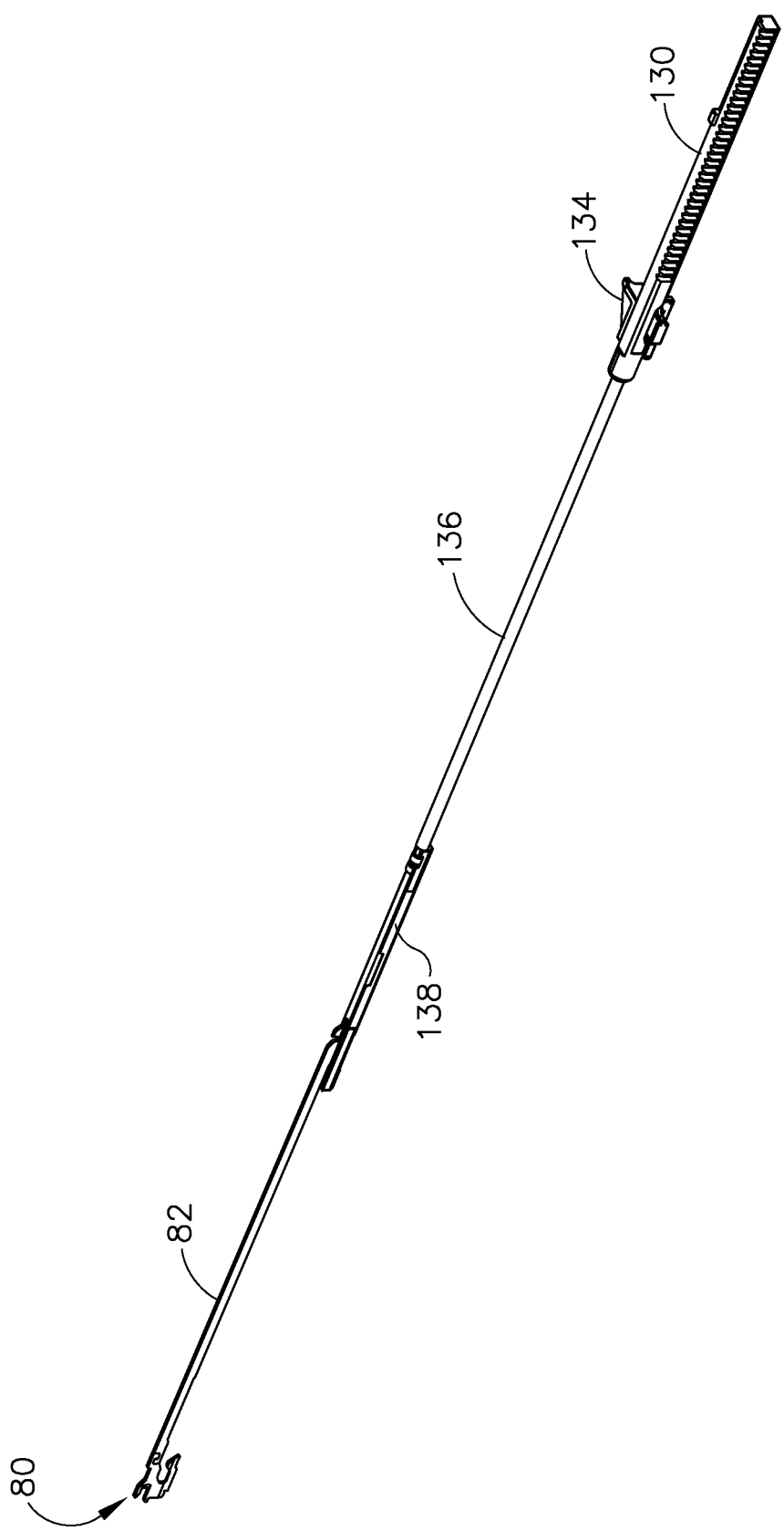
FIG. 12 depicts a perspective view of an elongate member from the drive assembly of FIG. 11, coupled with the firing beam.

Once firing beam (82) reaches a distal-most position (e.g., at the end of a cutting stroke), an end-of-stroke switch (112) is automatically switched to a closed position, reversing the polarity of the voltage applied to motor (102). This reverses the direction of rotation of motor (102), it being understood that the operator will have released firing trigger (26) at this stage of operation. In this operational state, current flows through a reverse direction indicator (114) (e.g., an LED, etc.) to provide a visual indication to the operator that motor (102) rotation has been reversed. In the present example, and as best seen in FIG. 12, a switch actuation arm (134) extends laterally from rack member (130), and is positioned to engage end-of-stroke switch (112) when firing beam (82) reaches a distal-most position (e.g., after tissue (90) has been severed and staples (77) have been driven into tissue (90)). Various other suitable ways in which end-of-stroke switch (112) may be automatically switched to a closed position when firing beam (82) reaches a distal-most position will be apparent to those of ordinary skill in the art in view of the teachings herein. Similarly, various suitable forms that reverse direction indicator (114) may take will be apparent to those of ordinary skill in the art in view of the teachings herein.

Handle assembly (20) of the present example also includes a manual return switch (116), which is also shown in circuit (100). In the present example, return switch is activated by actuating reverse switch (27), which is shown on handle assembly (20) in FIG. 1. Manual return switch (116) may provide functionality similar to end-of-stroke switch (112), reversing the polarity of the voltage applied to motor (102) to thereby reverse the direction of rotation of motor (102). Again, this reversal may be visually indicated through reverse direction indicator (114). In some versions, handle assembly (20) further includes a mechanical return feature that enables the operator to manually reverse firing beam (82) and thereby retract firing beam (82) mechanically. In the present example, this manual return feature comprises a lever that is covered by a removable panel (21) as shown in FIG. 1. Manual return switch (116) and the mechanical return feature are each configured to act as a "bailout" feature, enabling the operator to quickly begin retracting firing beam (82) proximally during a firing stroke. In other words, manual return switch (116) or the mechanical return feature may be actuated when firing beam (82) has only been partially advanced distally.

In some versions, one or more of switches (26, 106, 108, 112, 116) are in the form of microswitches. Other suitable forms will be apparent to those of ordinary skill in the art in view of the teachings herein. In addition to or in lieu of the foregoing, at least part of circuit (100) may be configured in accordance with at least some of the teachings of U.S. Pat. No. 8,210,411, entitled "Motor-Driven Surgical Instrument," issued Jul. 3, 2012, the disclosure of which is incorporated by reference herein.

Figure 10:
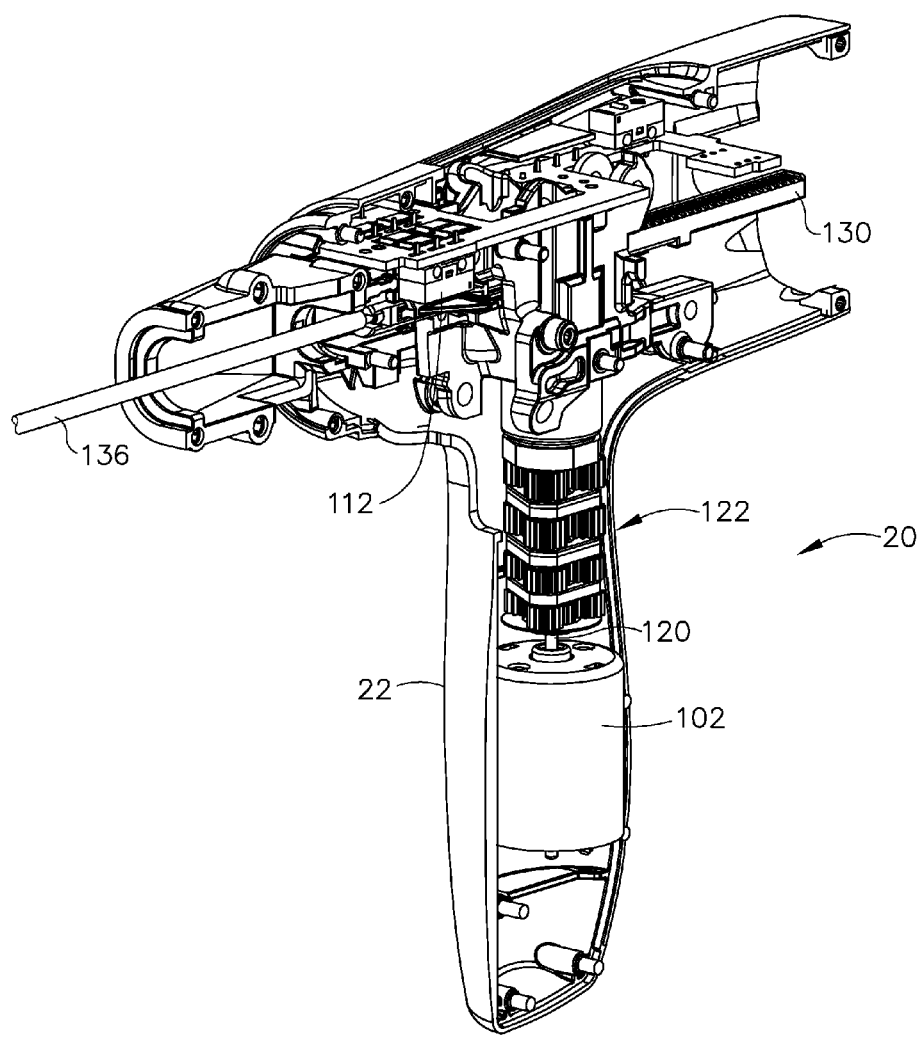
FIG. 10 depicts a perspective view of the handle assembly of the instrument of FIG. 1, with a housing half and some internal components removed.
Figure 11:
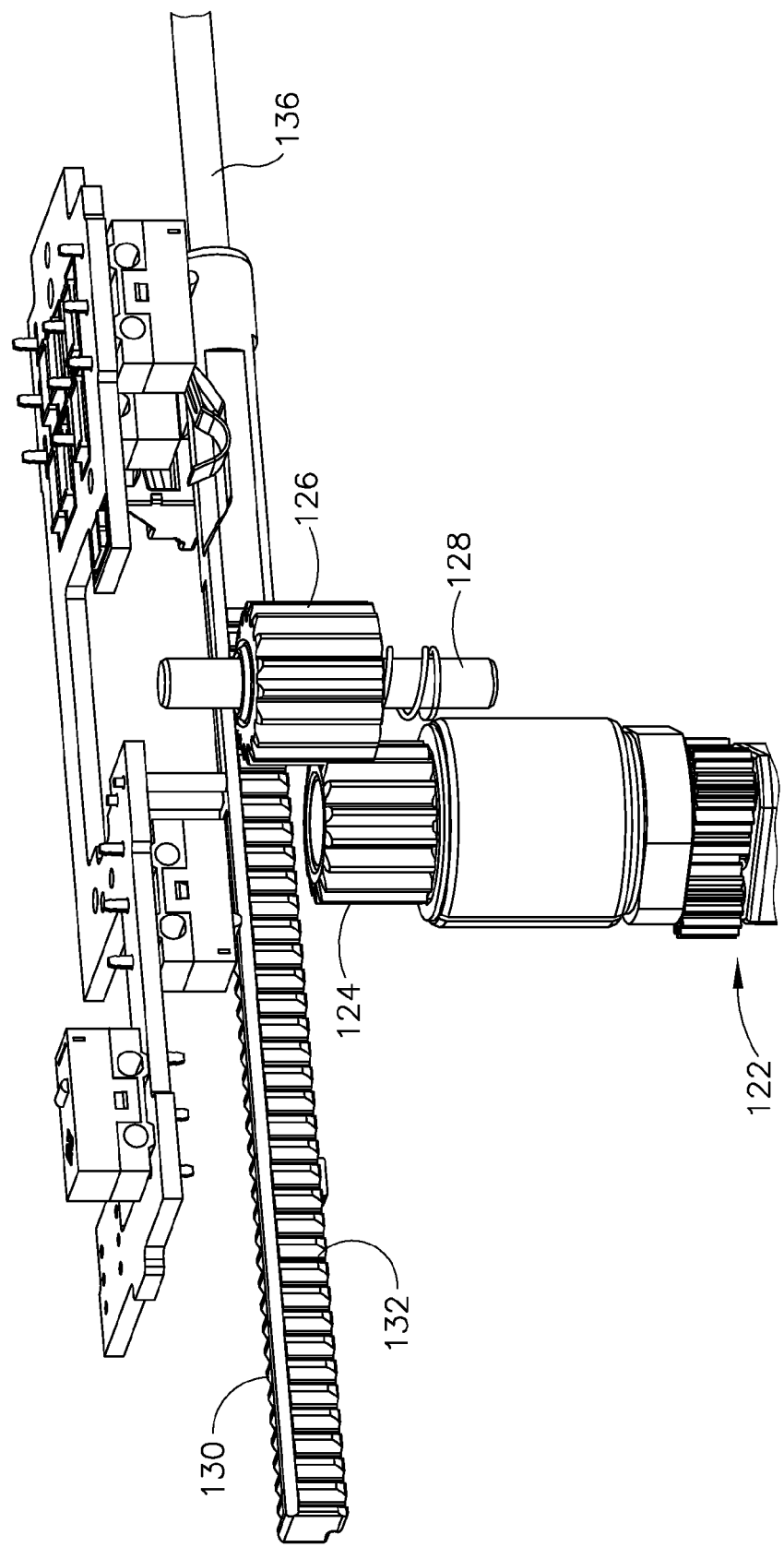
FIG. 11 depicts a perspective view of drive assembly components from the handle assembly of FIG. 10.

FIG. 10 shows motor (102) positioned within pistol grip (22) of handle assembly (20). Alternatively, motor (102) may be positioned elsewhere within handle assembly (20). Motor (102) has a drive shaft (120) that is coupled with a gear assembly (122). Thus, when motor (102) is activated, drive shaft (120) actuates gear assembly (122). As shown in FIG. 11, gear assembly (122) is in communication with a drive gear (124), which meshes with an idler pinion (126). Pinion (126) is disposed on a shaft (128) that is supported within handle assembly (20) and that is oriented parallel to drive shaft (120) of motor (102). Pinion (126) is further engaged with a rack member (130). In particular, pinion (126) meshes with teeth (132) at the proximal end of rack member (130). Rack member (130) is slidably supported in handle assembly (20). It should be understood from the foregoing that, when motor (102) is activated, the corresponding rotation of drive shaft (120) is communicated to pinion (126) via gear assembly (122), and the corresponding rotation of pinion (126) is converted to translation of rack member (130) by teeth (132). As shown in FIGS. 10-12, an elongate member (136) extends distally from rack member (130). As shown in FIG. 12, a coupling member (138) joins firing beam (82) with elongate member (136). Rack member (130), elongate member (136), coupling member (138), firing beam (82), and knife member (80) all translate together relative to handle assembly (20) in response to activation of motor (102). In other words, activation of motor (102) ultimately causes firing beam (82) to translate longitudinally, the direction of such translation depending on the direction of rotation of drive shaft (120).

It should be understood that a distal portion of elongate member (136), coupling member (138), and firing beam (82) extend through shaft assembly (30). A portion of firing beam (82) also extends through articulation section (34). In some versions, rack member (130), elongate member (136), and coupling member (138) are all substantially straight and rigid; while firing beam (82) has sufficient flexibility to bend at articulation section (34) and translate longitudinally through articulation section (34) when articulation section (34) is in a bent or articulated state.

In addition to or in lieu of the foregoing, the features operable to drive firing beam (82) may be configured in accordance with at least some of the teachings of U.S. Pat. No. 8,453,914, the disclosure of which is incorporated by reference herein. Other suitable components, features, and configurations for providing motorization of firing beam (82) will be apparent to those of ordinary skill in the art in view of the teachings herein. It should also be understood that some other versions may provide manual driving of firing beam (82), such that a motor may be omitted. By way of example only, firing beam (82) may be actuated in accordance with at least some of the teachings of any other reference cited herein.

Figure 8:
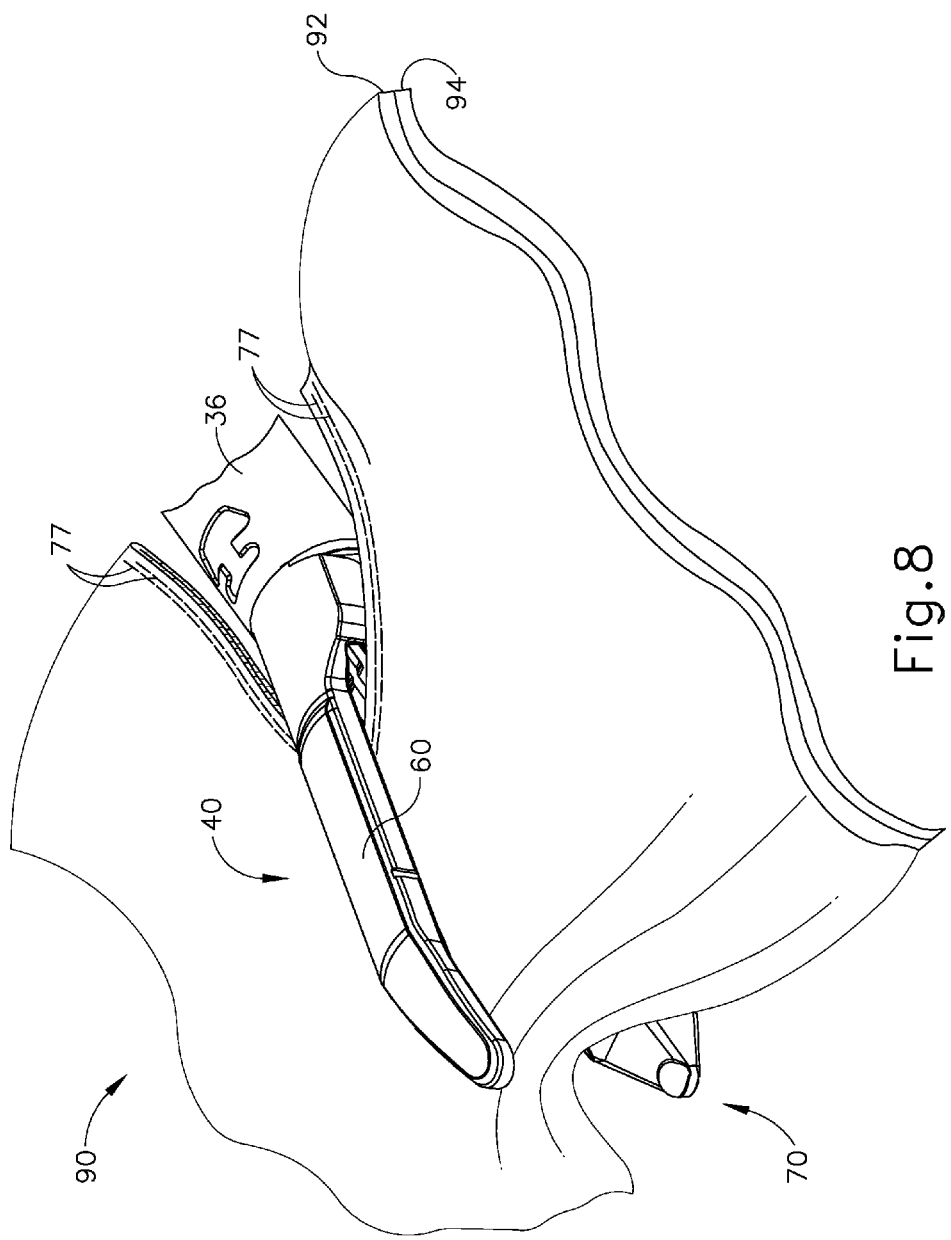
FIG. 8 depicts a perspective view of the end effector of FIG. 3, positioned at tissue and having been actuated once in the tissue.

FIG. 8 shows end effector (40) having been actuated through a single stroke through tissue (90). As shown, cutting edge (84) (obscured in FIG. 8) has cut through tissue (90), while staple drivers (75) have driven two alternating rows of staples (77) through the tissue (90) on each side of the cut line produced by cutting edge (84). Staples (77) are all oriented substantially parallel to the cut line in this example, though it should be understood that staples (77) may be positioned at any suitable orientations. In the present example, end effector (40) is withdrawn from the trocar after the first stroke is complete, the spent staple cartridge (70) is replaced with a new staple cartridge (70), and end effector (40) is then again inserted through the trocar to reach the stapling site for further cutting and stapling. This process may be repeated until the desired amount of cuts and staples (77) have been provided. Anvil (60) may need to be closed to facilitate insertion and withdrawal through the trocar; and anvil (60) may need to be opened to facilitate replacement of staple cartridge (70).

It should be understood that cutting edge (84) may sever tissue substantially contemporaneously with staples (77) being driven through tissue during each actuation stroke. In the present example, cutting edge (84) just slightly lags behind driving of staples (77), such that a staple (47) is driven through the tissue just before cutting edge (84) passes through the same region of tissue, though it should be understood that this order may be reversed or that cutting edge (84) may be directly synchronized with adjacent staples (77). While FIG. 8 shows end effector (40) being actuated in two layers (92, 94) of tissue (90), it should be understood that end effector (40) may be actuated through a single layer of tissue (90) or more than two layers (92, 94) of tissue. It should also be understood that the formation and positioning of staples (77) adjacent to the cut line produced by cutting edge (84) may substantially seal the tissue at the cut line, thereby reducing or preventing bleeding and/or leaking of other bodily fluids at the cut line. Furthermore, while FIG. 8 shows end effector (40) being actuated in two substantially flat, apposed planar layers (92, 94) of tissue, it should be understood that end effector (40) may also be actuated across a tubular structure such as a blood vessel, a section of the gastrointestinal tract, etc. FIG. 8 should therefore not be viewed as demonstrating any limitation on the contemplated uses for end effector (40). Various suitable settings and procedures in which instrument (10) may be used will be apparent to those of ordinary skill in the art in view of the teachings herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Alternative Shaft Assembly

It will be appreciated that as a user urges instrument (10) into a surgical region, it may be desirable to approach the tissue to be clamped, stapled, or cut, from a particular angle. For instance, once end effector (40) of instrument (10) is inserted through a trocar, thoracotomy, or other passageway for entering a surgical area, the tissue that the user wishes to target may be positioned out of reach or at an askew angle in relation to end effector (40) that is aligned with longitudinal axis (LA) of shaft assembly (30). Thus, it may be desirable for portions of instrument (10), such as end effector (40), to articulate relative to longitudinal axis (LA) of shaft assembly (30) at an angle (a) (as seen in phantom in FIG. 1) such that the user can position anvil (60) and lower jaw (50) of end effector (40) to squarely or perpendicularly clamp against a vessel or other tissue. It will further be understood that articulating end effector (40) to squarely position end effector (40) against tissue may promote full seating and clamping of the tissue prior to cutting and stapling tissue. In addition to articulating, it may be desirable for end effector (40) to be selectively locked in a straight or articulated position such that a constant manual bias by the user is not necessary to prevent end effector (40) from pivoting or bending at articulation section (34). It may also be desirable to automatically lock upon articulation, without requiring actuations of a separate articulation locking feature.

Figure 13A:
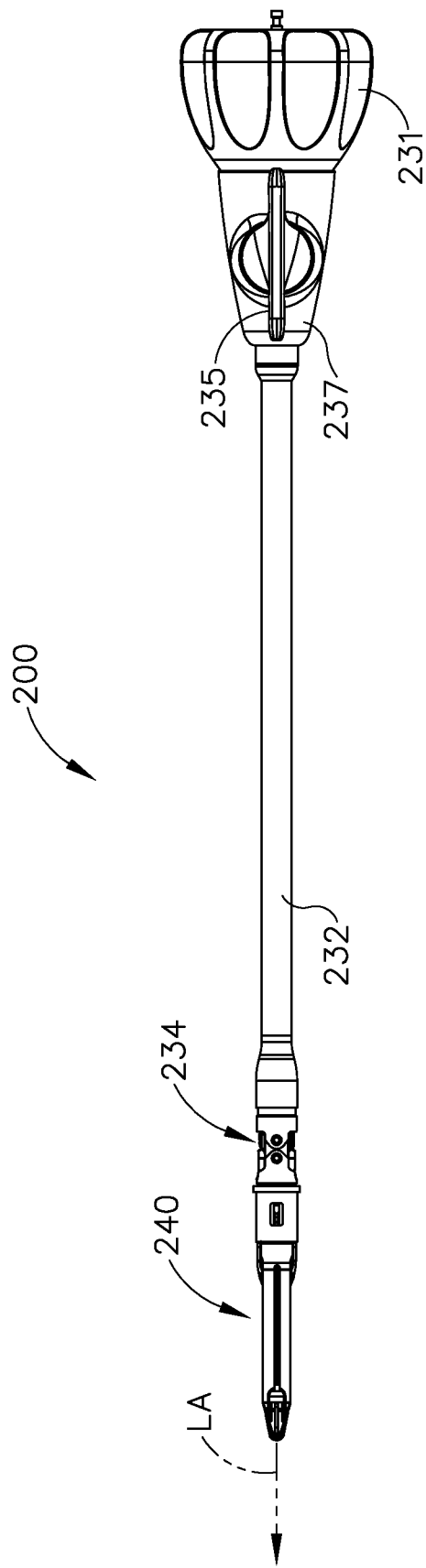
FIG. 13A depicts a top, plan view of an exemplary alternative shaft assembly that may be incorporated into the instrument of FIG. 1, with the end effector in a first position.

FIG. 13A depicts an exemplary alternative shaft assembly (200) that may be readily incorporated with instrument (10) of FIG. 1. Shaft assembly (200) provides articulation and selective locking of articulation angles, as will be described in greater detail below. Shaft assembly (200) of the present example comprises a rotation knob (231), articulation control knob (235), and an end effector (240). Shaft assembly (200) also comprises end effector (240) positioned distally in relation to a closure tube (232). End effector (240) includes an articulation joint (234) which allows end effector (240) to articulate laterally as will be described in further detail below. End effector (240) is substantially identical to end effector (40) of FIG. 1 except as otherwise described below.

Rotation knob (231) may be rotatably coupled with handle assembly (20) of FIG. 1 or any other suitable component (e.g., robotic control interface, etc.). Rotation knob (231) is operable to rotate shaft assembly (200) (including articulation control knob (235) and end effector (240)) about the longitudinal axis (LA) defined by shaft assembly (200), relative to handle portion (20) (or relative to whatever else rotation knob (231) is rotatably coupled with). This may be useful in positioning end effector (240) at a desired angular orientation about the longitudinal axis (LA).

A. Exemplary Articulation Control Features

Figure 13B:
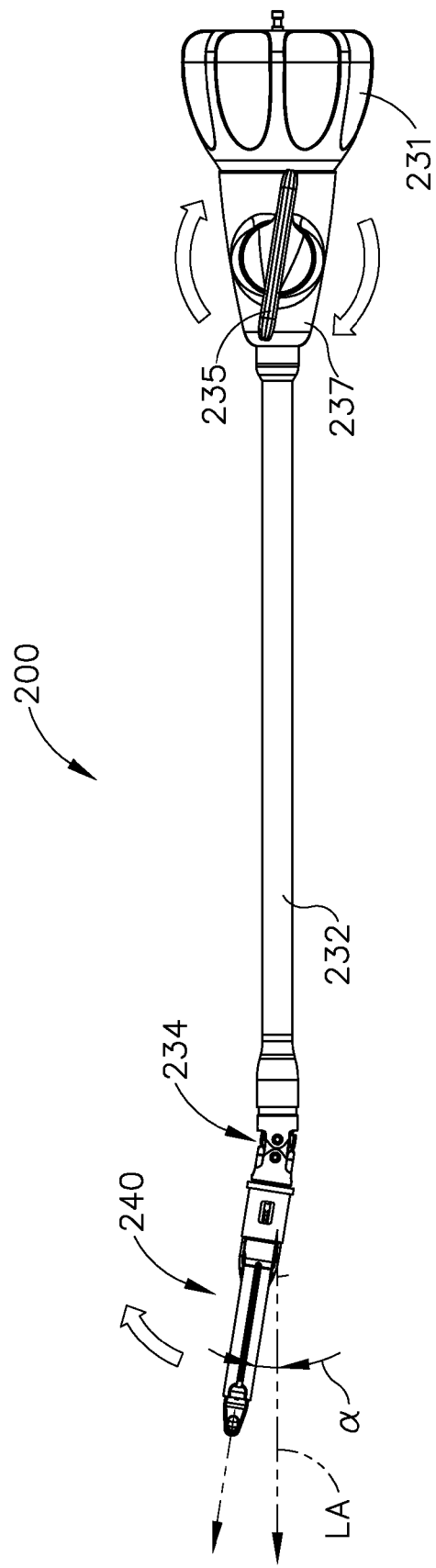
FIG. 13B depicts a top, plan view of the shaft assembly of FIG. 13A with the end effector in a second articulated position.

Articulation control knob (235) is partially contained within an articulation control knob casing (237). Casing (237) leads to closure tube (232). FIGS. 13A-B show shaft assembly (200) and an exemplary movement of end effector (240) in response to turning of articulation control knob (235). FIG. 13A shows articulation control knob (235) in a first position where articulation control knob (235) and end effector (240) are both generally aligned along the longitudinal axis (LA) of shaft assembly (200). The user may then manually rotate articulation control knob (235) clockwise as seen in FIG. 13B to a second position. In response to the rotation of articulation control knob (235), end effector (240) pivots or bends at articulation joint (234). as seen in FIG. 16B, to an articulation angle (a). In the present example, end effector (240) articulates generally in the direction of the rotation of articulation control knob (235), though it will be understood that end effector (240) may be configured to bend in the opposite direction of the rotation of articulation control knob (235). In other words, when articulation control knob (235) is rotated clockwise, end effector (240) laterally pivots clockwise as shown in FIG. 13B but could be configured in some versions to pivot counter clockwise. FIG. 13B shows end effector (240) laterally pivoting clockwise slightly. It will be understood that articulation control knob (235) may be rotated further to cause end effector (240) to laterally articulate further at articulation joint (234) to any suitable angle (a). For instance, end effector (240) may pivot until an approximately 90° angle is formed across articulation joint (234). In some versions, end effector (240) may be operable to pivot even further such that end effector (240) forms an acute angle in relation to tube (232). Other suitable variations of end effector (240) pivoting will be apparent to one of ordinary skill in the art in view of the teachings herein. It should also be understood that articulation control knob (235) may define the same angle with the longidunal axis (LA) as the articulation angle (a) defined between end effector (240) and the longidunal axis (LA). Such complementary angling may provide the operator with visual feedback exterior to the patient, indicating the articulation angle (a) of end effector (240).

The mechanics of the articulation of end effector (240) will be discussed in further detail below. It will be appreciated that articulation control knob (235) may be rotated in the counter clockwise direction to cause end effector (240) to articulate in a counter clockwise manner. Thus, depending on the desired direction and/or amount of articulation of end effector (240), the user can simply rotate articulation control knob (235) of varying degrees in the direction that the user wishes end effector (240) to articulate to cause varying degrees of articulation of end effector (240).

Figure 14:
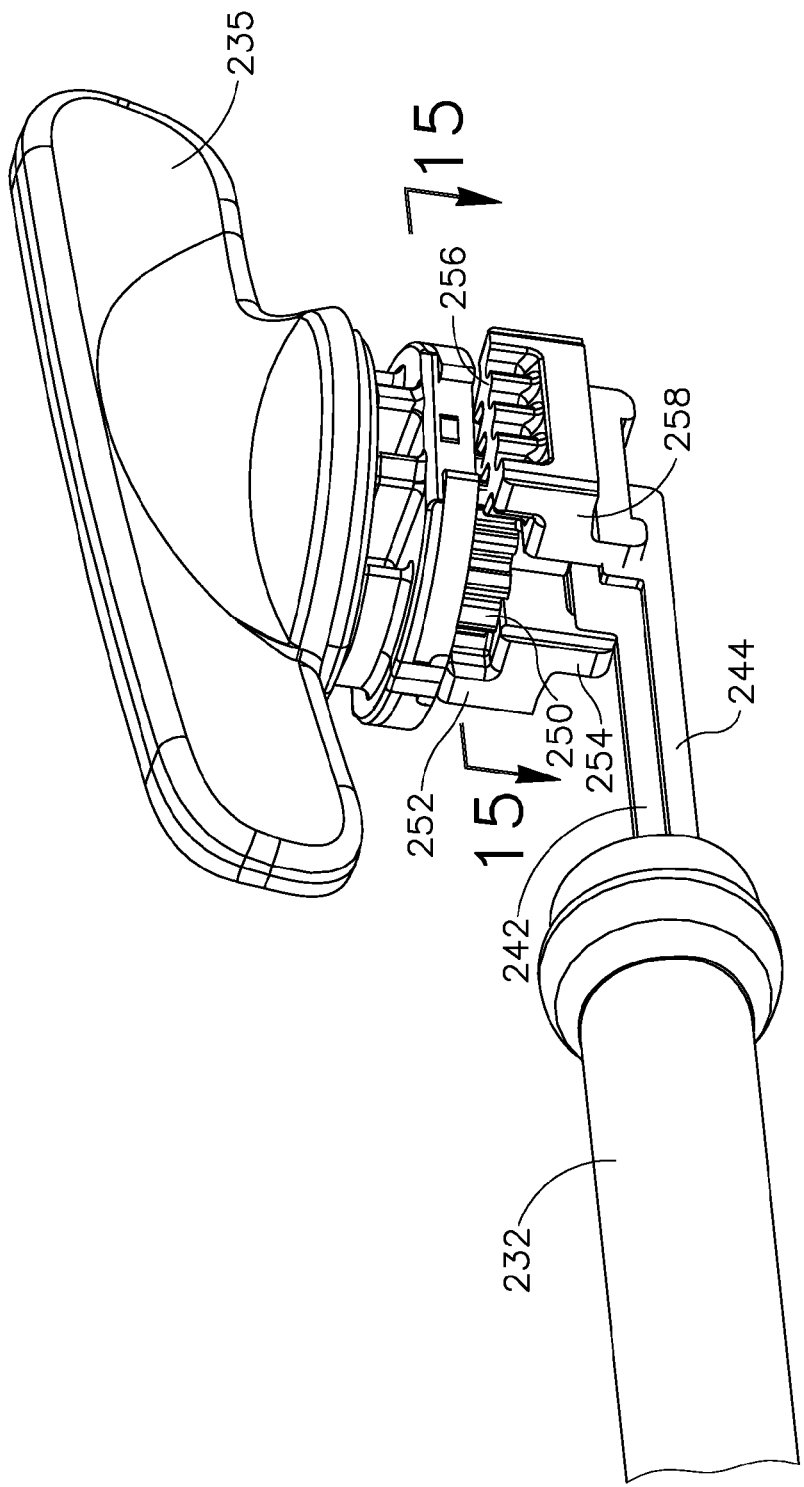
FIG. 14 depicts a perspective view of the proximal end of the shaft assembly of FIG. 13A showing the articulation knob and internal kinematic components.

FIG. 14 shows articulation control knob (235) with casing (237) removed to better show the inner workings of articulation control knob (235). Articulation control knob (235) is in communication with an articulation pinion (250). Articulation pinion (250) is in communication with a first rack (252) and a second rack (256). First rack (252) is in communication with a first arm (242) through a first intermediate block (254), whereas second rack (256) is in communication with a second arm (244) through a second intermediate block (258). Arms (242, 244) are substantially parallel to each other in the present example. In particular, the proximal portions of arms (242, 244) (as shown in FIG. 18 and the portions of arms (242, 244) that extend through shaft assembly (200) are parallel to each other, though the proximal ends of arms (242, 244) flare slightly outwardly. Since arms (242, 244) are parallel to each other along nearly their entire length (i.e., except for the distal-most portions), arms (242, 244) may be readily recognized by those skilled in the art as being "substantially parallel" to each other.

Figure 15:
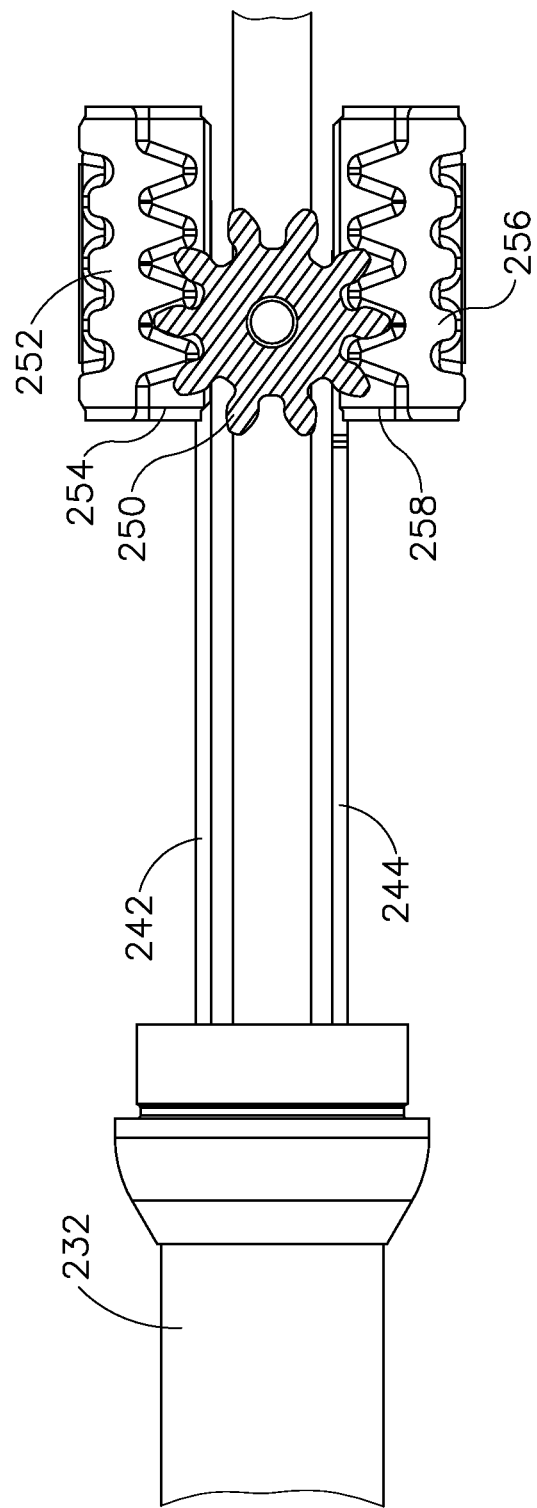
FIG. 15 depicts a top cross-sectional view of the proximal end of the shaft assembly of FIG. 13A taken along line 15-15 of FIG. 14.

Articulation control knob (235) is unitarily coupled to articulation pinion (250). As a result, when the user turns articulation control knob (235), articulation pinion (250) rotates together with articulation control knob (235). As articulation pinion (250) rotates, articulation pinion translates first rack (252) and second rack (256) accordingly in opposing directions. For instance, as seen in FIG. 15, articulation pinion (250) is in communication with first rack (252) and second rack (256) such that if articulation pinion (250) rotates clockwise, first rack (252) retracts proximally away from end effector (240) whereas second rack (256) advances distally toward end effector (240). Furthermore, when articulation pinion (250) rotates counter-clockwise, first rack (252) advances distally toward end effector (240) and second rack (256) retracts proximally away from end effector (240). As first rack (252) advances and retracts, first arm (242) advances and retracts in a similar manner. Similarly, as second rack (256) advances and retracts, second arm (244) also advances and retracts with second rack (256). Thus, rotating actuation control knob (235), which is connected to articulation pinion (250), causes first arm (242) and second arm (244) to move back and forth with first rack (252) and second rack (256). Movement of first arm (242) and second arm (244) is operable to cause movement of other components in end effector (240), as will be discussed in greater detail below.

Figure 16:
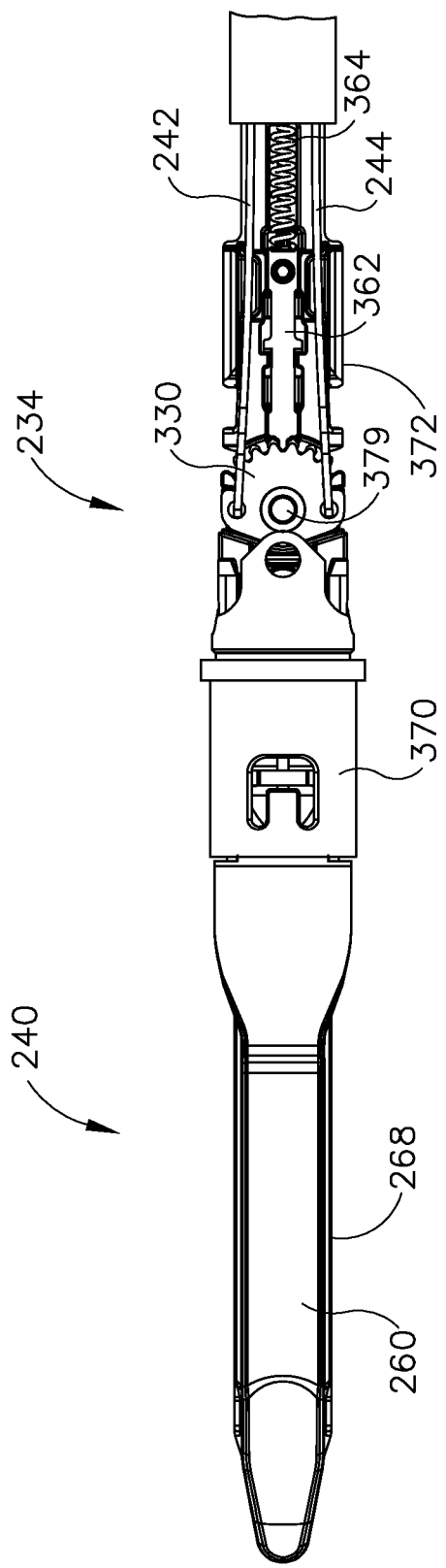
FIG. 16 depicts a top, plan view of the shaft assembly of FIG. 13A in a neutral position.

FIG. 16 shows a larger view of end effector (240), including anvil (260). First arm (242) and second arm (244) are in communication with a first cam member (330), which is pivotally disposed about a pin (379). As a result, advancing and retracting first arm (242) and second arm (244) causes first cam member (370) to rotate about cam holding pin (379), as will be described in further detail below.

Figure 17:
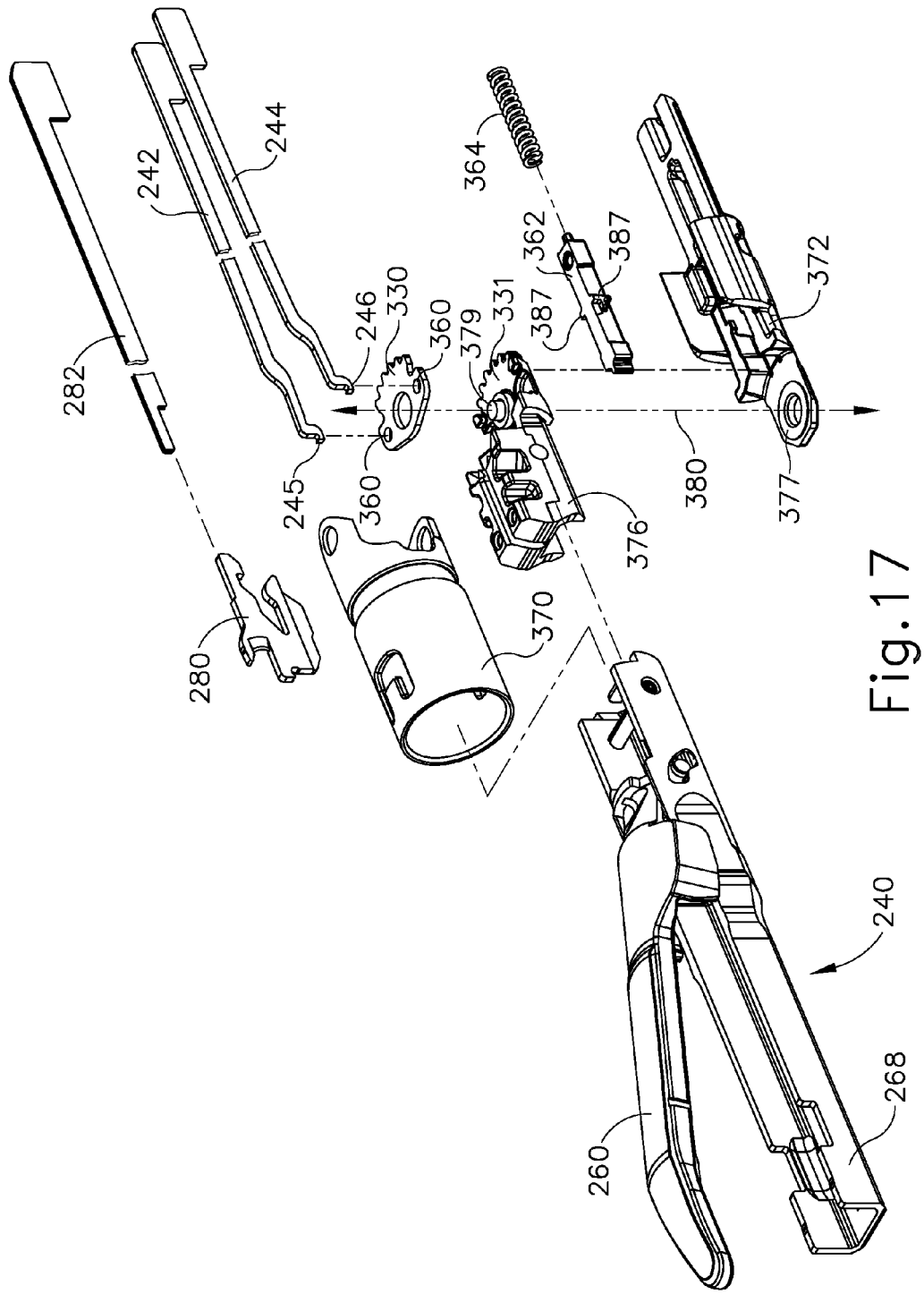
FIG. 17 depicts a perspective, exploded view of the end effector and the articulation joint of the shaft assembly of FIG. 13A.

FIG. 17 shows an exploded view of articulation joint (234). End effector (240) is disposed at the distal end of articulation joint (234). End effector (240) comprises an anvil (260) and lower jaw (268). It will be appreciated that end effector (240) is substantially similar to end effector (40) of FIG. 1. Similar to lower jaw (50) of end effector (40), lower jaw (268) may receive a staple cartridge (not shown) which may be substantially similar to staple cartridge (70). Additionally, similar to end effector (40) as described above, anvil (260) is driven toward lower jaw (268) by advancing a closure ring (236) distally relative to end effector (240). Closure ring (236) is driven longitudinally relative to end effector (240) based on translation of closure tube (232). Translation of closure tube (232) is communicated to closure ring (236) via articulation joint (234). Functionally, anvil (260) and lower jaw (268) are substantially similar to anvil (60) and lower jaw (50) of end effector (40) with anvil (260) and lower jaw (268) working cooperatively to contemporaneously sever and staple tissue as shown in FIG. 8 and described above.

Articulation joint (234) comprises first cam member (330), second cam member (331), cam holding body (376), joint base (372), a lock bar (262) and a spring (364). First arm (242) distally terminates in a first hook (245), while second arm (244) distally terminates in a second hook (246). Hooks (245, 246) are in communication with cam openings (360) of first cam member (330). As a result, when first arm (242) adavances toward end effector (240) and second arm (244) retracts, first cam member (330) rotates counter clockwise about holding pin (379). When first arm (242) instead retracts and second arm (244) advances toward end effector (240), first cam member (330) rotates clockwise about holding pin (379). Thus, as arms (242, 244) push and pull on cam openings (360) via hooks (245, 246) in an opposing fashion, first cam member (330) rotates accordingly as just described.

First cam member (330) is stacked on a second cam member (331). Second cam member (331) and cam holding pin (379) are unitary features of cam holding body (376). In some versions, second cam member (331) may be separately constructed and fixedly coupled with cam holding body (376), such that as second cam member (331) rotates, cam holding body (376) rotates. Cam holding pin (379) is coaxially aligned with base opening (377) of joint base (372) along a pivot axis (380). Thus, first cam member (330) is rotatable about pivot axis (380), relative to second cam member (231) and cam holding body (376). Lock bar (262) is in selective communication with first cam member (330) and second cam member (331), which will be described in greater detail below. Lock bar (262) is further in communication with spring (364), which distally biases lock bar (262). Joint base (372) is shaped to provide a seat and/or channel for lock bar (262) to advance in. Lock bar (262) further includes a pair of bosses (387) operable to engage joint base (372) to restrict distal motion of lock bar (262).

B. Exemplary Articulation of the Shaft Assembly

As discussed above, actuating articulation control knob (235) causes opposing advancement and retraction of arms (242, 244). It will be understood that this motion of arms (242, 244) rotates first cam member (330) about cam holding pin (279). As a result of rotating first cam member (330), second cam member (331) rotates with cam holding body (376. Thus, articulation joint (234) articulates, thereby pivoting end effector (240) at articulation joint (234). In particular, cam holding pin (379) and base opening (374) define a pivot axis (380), which is generally perpendicular to the longitudinal axis (LA) as noted above. End effector (240) pivots about pivot axis (380) in response to the rotation of first cam member (330), which drives second cam member (331) as will be discussed below. In other words, pivot axis (380) serves as an axis for articulation of end effector (240) relative to shaft assembly (200). FIGS. 18A-E show the details of rotating first cam member (330) to drive the articulation of end effector (240).

Figure 18A:
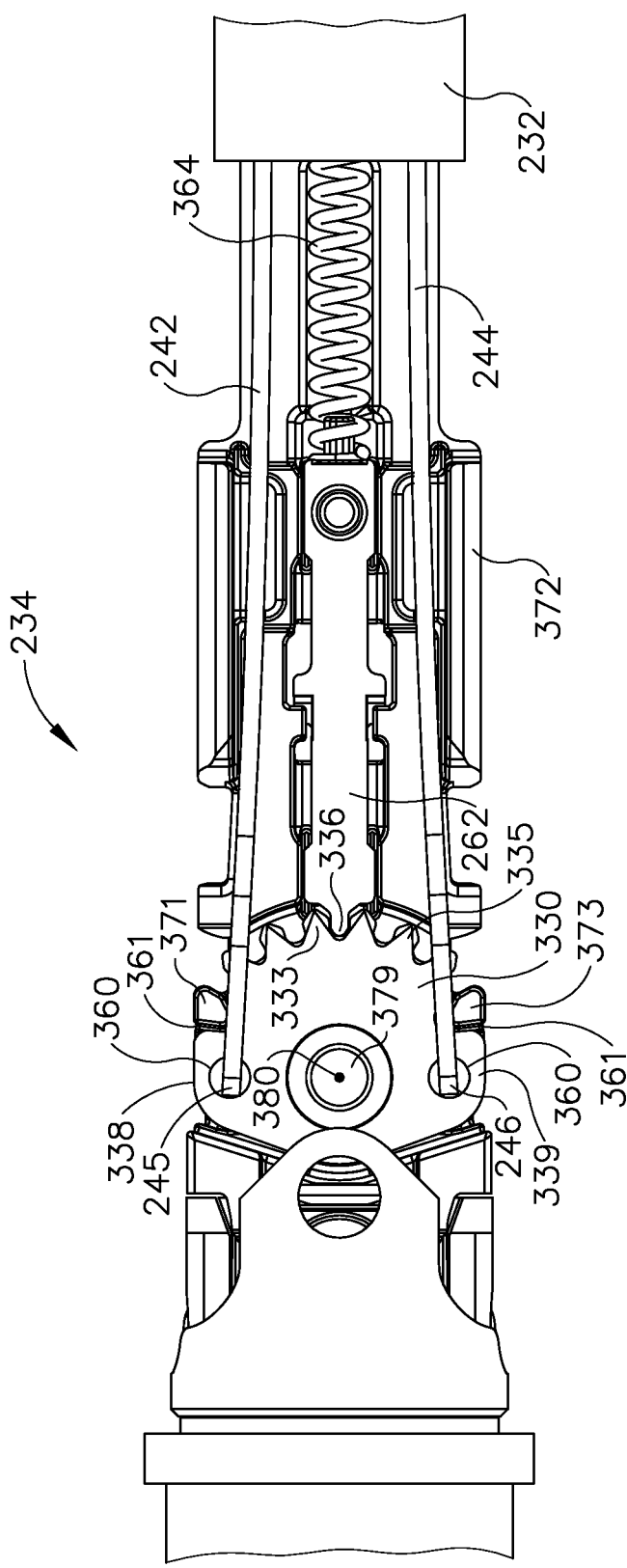
FIG. 18A depicts a top, partially internal view of the articulation joint of the shaft assembly of FIG. 13A in a first position.

FIG. 18A shows articulation joint (234) in a first position. Lock bar (262) is distally biased to engage second cam member (331). In particular, the distal end of lock bar (262) comprises a lock tooth (336) that fits between first cam teeth (333) and second cam teeth (335) and abuts second cam member (331), which can be seen in further detail in FIG. 19. As a result of the distal bias provided by spring (364), lock tooth (336) acts as a positive lock and thus maintains the rotational position of second cam member (331). By maintaining the rotational position of second cam member (331), lock bar (262) maintains the angular position of end effector (240) about pivot axis (380), thereby maintaining any articulation angle (a). First cam member (330) comprises a pair of cam wings (338, 339), and cam holding body (376) comprises a pair of bosses (371, 373). Bosses (371, 373) are unitary features of second cam member (331), such that as bosses (371, 373) rotate, second cam member (331) also rotates. It will be appreciated that in the first position of FIG. 18A, cam wings (338, 339) and bosses (371, 373) are not in contact. The interaction involving contact between cam wings (338, 339) and bosses (371, 373) will be described in further detail below with reference to FIGS. 18B-E. During a surgical operation, the user may guide shaft assembly (200) through a passageway (e.g., trocar, thoracotomy, etc.) to reach the surgical area with end effector (240) in a straightened position as shown in FIG. 18A.

FIG. 19 shows an enlarged view of lock tooth (336) in the position shown in FIG. 18A. As can be seen, lock tooth (336) has generally straight parallel sides (386) that are configured to fit between first cam teeth (333) and second cam teeth (335). The distal end of lock tooth (336) has a rounded tip (385) with angled sides (381) leading to parallel sides (386). Each tooth (335) of second cam teeth (335) comprises generally straight parallel sides (383) and angled sides (384). Parallel sides (383) are configured to engage parallel sides (386) of lock tooth (336) to prevent lock tooth (336) from riding along second cam teeth (335) without assistance from first cam member (330). This engagement between at least one side (383) and at least one side (386) also prevents cam holding body (376) from rotating about pivot axis (380), thereby preventing end effector (240) from pivoting at articulation joint (234).

Figure 18B:
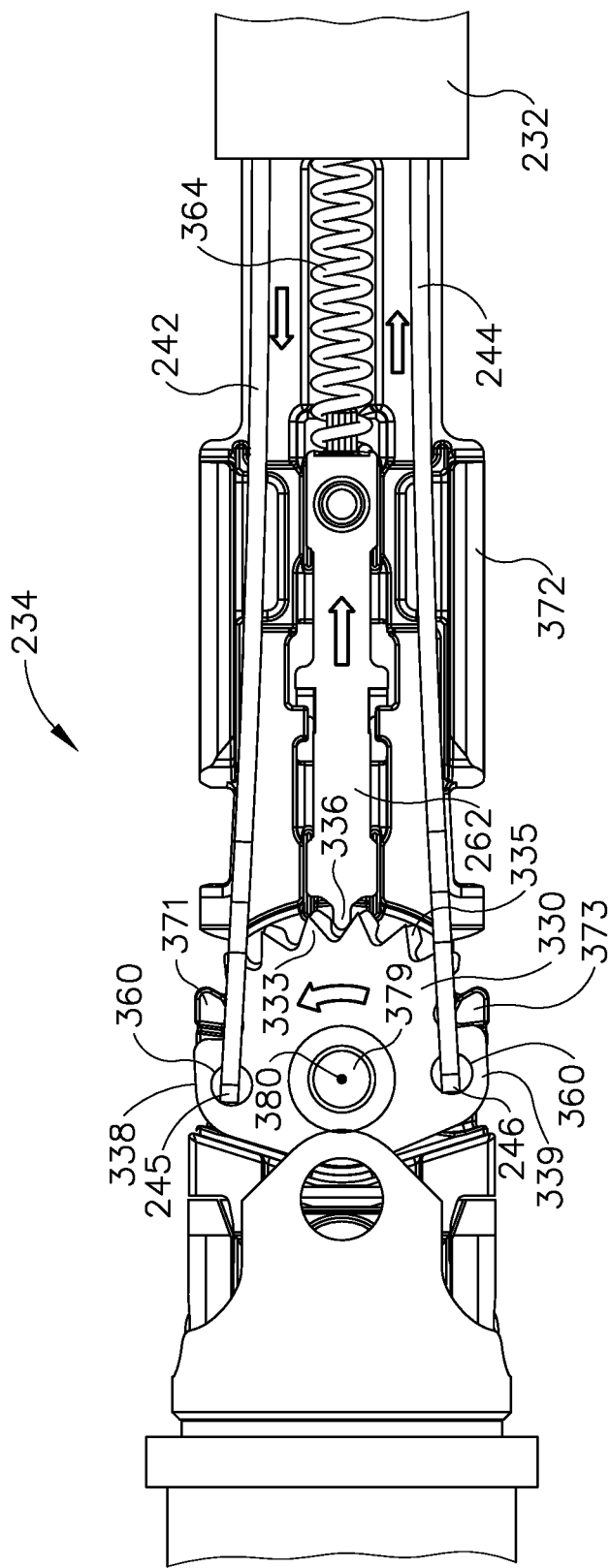
FIG. 18B depicts a top, partially internal view of the articulation joint of the shaft assembly of FIG. 13A with the first and second arms rotating a first cam member.
Figure 18C:
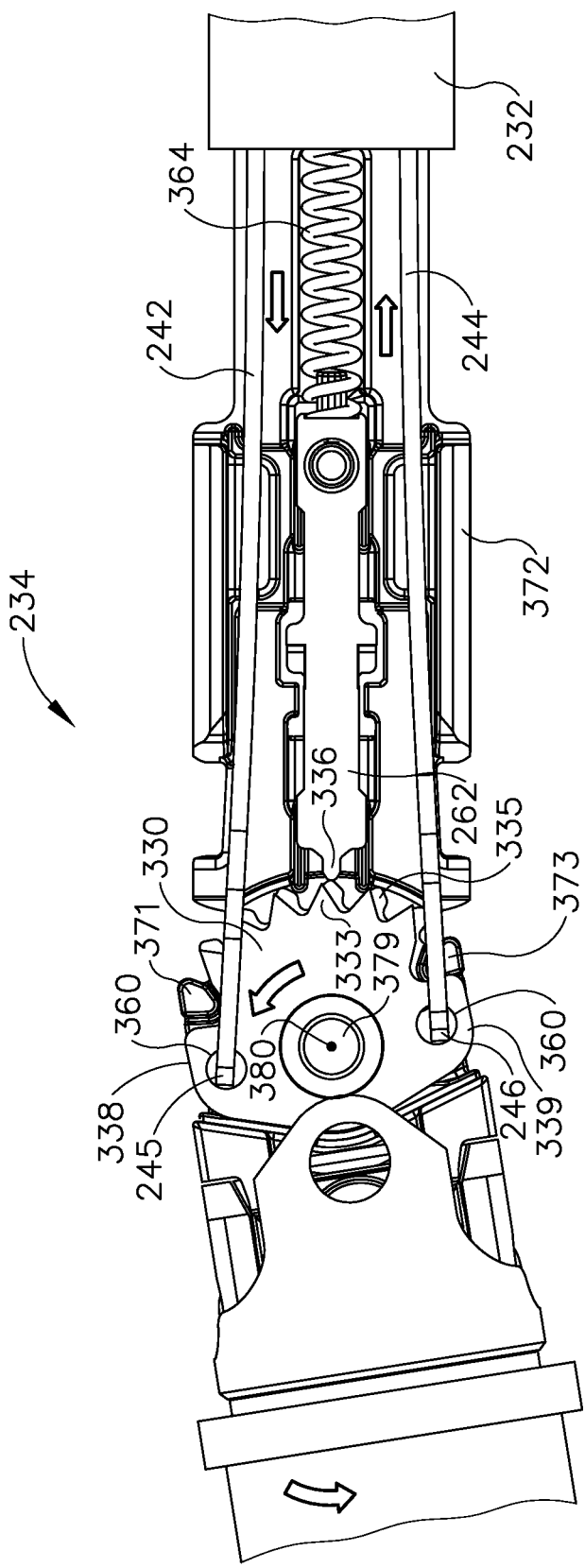
FIG. 18C depicts a top, partially internal view of the articulation joint of the shaft assembly of FIG. 13A with the first and second arms rotating a second cam member and the first cam member further.

Once first cam member (330) rotates as shown in FIGS. 18B-C and as will be described in greater detail below, a triangular tooth (333) of first cam member (330) will cam against angled sides (381), and will thereby dive lock bar (262) proximally in response to first cam (330) rotating. It should be understood that tooth (333) may have a variety of different shapes other than triangular. Some exemplary alternative shapes will be described in greater detail below, while others will be apparent to those of ordinary skill in the art in view of the teachings herein. Lock tooth (336) moves proximally sufficiently such that angled sides (381) of lock tooth (336) can eventually engage and ride along angled sides (384) of second cam teeth (335) as first cam member (330) continues to rotate and as second cam member (331) rotates. This provides further camming action to drive lock bar (262) proximally. Once lock tooth (336) traverses angled sides (384) of second cam teeth (335), then lock tooth (336) returns distally to a position between the next pair of first cam teeth (333) and second cam teeth (335) similar to the positioning shown in FIG. 19. For illustrative purposes, advancing lock tooth (336) between one set of first cam teeth (333) and second cam teeth (335) may be considered one articulation increment. As lock tooth (336) distally advances, lock tooth (336) strikes second cam member (331) between second cam teeth (335). It will be understood that lock tooth (336) need not necessarily extend far enough to strike second cam member (331). For instance, lock tooth (336) may only extend distally such that parallel sides (383) prevent lock tooth (336) from riding along second cam member (331) without assistance from first cam teeth (333). In the illustrated version, bosses (387) engage joint base (382) to prevent further distal motion of lock bar (262).

As noted above, the operator may wish to pivot end effector (240) at articulation joint (234) to better position end effector (240) in relation to targeted tissue. FIG. 18B shows a second stage of actuation for articulation joint (234) to move to in response to turning articulation control knob (235) shown in FIG. 14. In the illustrated version, the user has turned articulation knob (235) counter clockwise, which rotates articulation pinion (250) as well. As articulation pinion (250) rotates counter clockwise, first rack (252) moves distally and second rack (256) moves proximally in relation to end effector (240). Accordingly, first arm (242) and second arm (244) as shown in FIG. 18B move such that first arm (242) advances toward end effector (240) and second arm (244) retracts away from end effector (240). It will be appreciated that the distal portions of first arm (242) and second arm (244) of the illustrated version are not positioned parallel in relation to each other. Instead, first arm (242) and second arm (244) are obliquely angled in relation to each other, though it will be understood that first arm (242) and second arm (244) could be positioned parallel to each other.

Movement of arms (242, 244) as seen in FIG. 18B causes first cam member (330) to rotate counter clockwise about pivot axis (380). As first cam member (330) rotates, two actions occur in a generally simultaneous manner. First, cam teeth (330) have a triangular shape that urges lock bar (262) proximally away from end effector (240) through a camming action as a result of first cam teeth (333) engaging angled sides (381). Again, teeth (333) may have a variety of different shapes other than triangular. Spring (364) compresses to accommodate proximal motion of lock bar (262). As a result, rounded tip (385) moves proximally sufficient to traverse parallel sides (383). Additionally, cam wings (338, 339) rotate counter clockwise with first cam member (330). As a result of the rotation, cam wing (339) removes gap (361) between boss (373) and engages boss (373). Meanwhile, cam wing (338) moves rotationally away from boss (371). It will be understood that while first cam member (330) and lock bar (262) have moved in response to the movement of arms (242, 244) during the transition from the configuration shown in FIG. 18A to the configuration shown in FIG. 18B, second cam member (331) and accordingly end effector (240) have not yet moved. Thus, end effector (240) remains in a straight orientation at this stage.

FIG. 18C shows a third stage of actuation of articulation joint (234). It will be understood that the user continues to rotate articulation control knob (235) in an effort to articulate end effector (240). Arms (242, 244) continue to move such that first arm (242) moves distally and second arm (244) moves proximally. Movement of arms (242, 244) continues to rotate first cam member (330), which causes cam wing (339) to rotationally move further thereby urging boss (373) to rotationally move as well. Since boss (273) is unitary with second cam member (331), second cam member (331) begins to rotate. As second cam member rotates (331), lock bar (262) moves further proximally as a result of angled sides (384) camming against angled sides (381) of lock tooth (336). Thus, lock tooth (236) rides along second cam teeth (335). Second cam member (331) rotates until tip (388) of second cam member (331) engages rounded tip (385). Second cam teeth (335) have parallel sides (383) such that angled edges (381) of lock tooth (336) can engage angled sides (284) only after first cam teeth (333) urges lock tooth (336) proximally such that rounded tip (385) traverses parallel sides (383). Prior to riding along first cam teeth (333), lock tooth (336) is generally unable to ride along second cam teeth (335) due to parallel sides (383) engaging parallel sides (386). It will further be appreciated that as lock tooth (336) rides along angled sides (384), lock tooth (336) disengages first cam teeth (333). As also seen in FIG. 18C, lock bar (262) and lock tooth (336) have moved to a proximal most position with just second cam teeth tip (388) being in contact with lock tooth (336). Also as a result of rotation of second cam member (331), cam holding body (376) and accordingly, closure ring (236), which leads to end effector (240), articulate in a counter clockwise direction.

Figure 18D:
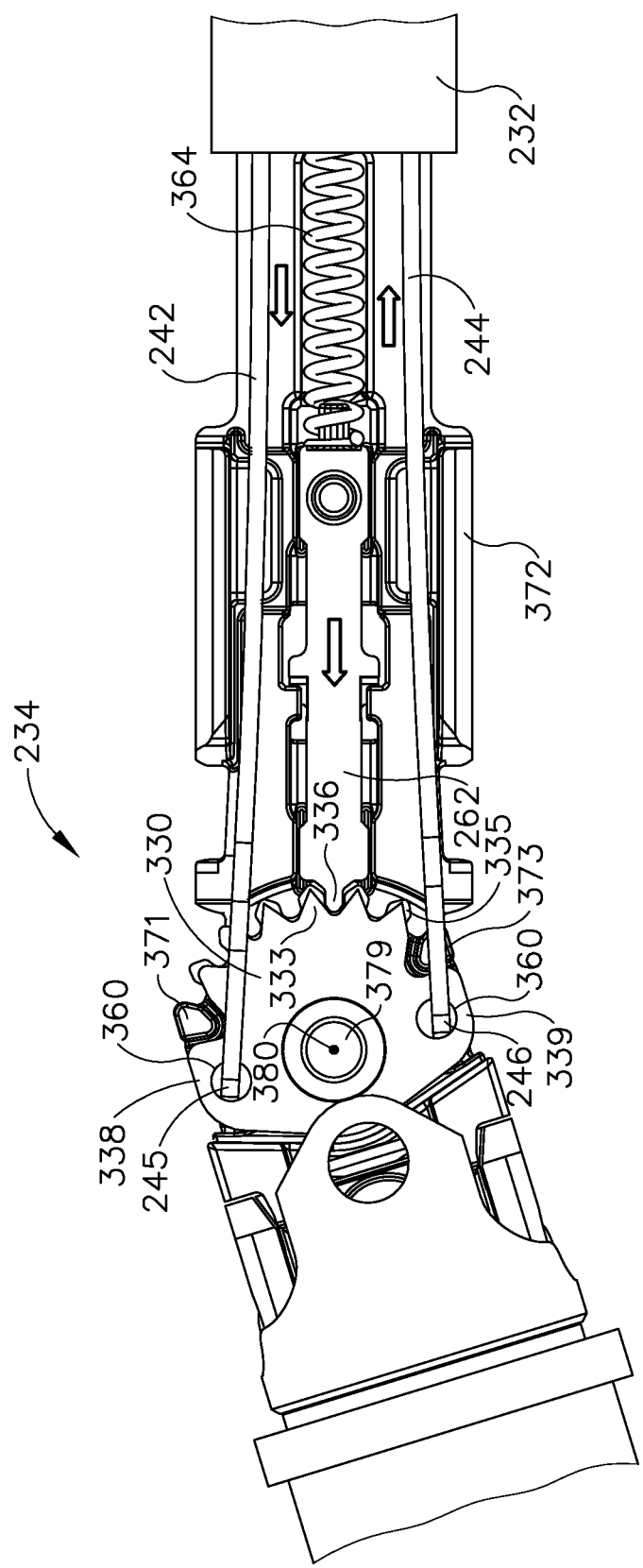
FIG. 18D depicts a top, partially internal view of the articulation joint of the shaft assembly of FIG. 13A with a lock bar resiliently positioning a lock tooth between teeth of the first cam member and the second cam member.

FIG. 18D shows a fourth stage of actuation for articulation joint (234). Once again, it will be understood that user is continuing to rotate articulation control knob (235) in an effort to cause further articulation of end effector (240). Arms (242, 244) continue to move such that first arm (242) moves distally further and second arm (244) moves proximally further. Movement of arms (242, 244) continues to rotate first cam member (330), which causes cam wing (339) to push boss (373) rotationally further. Lock tooth (336)

continues to ride along second cam teeth (335) until the distal bias caused by spring (364) urges lock bar (262) into the position shown in FIG. 18D. It will be appreciated that when lock bar (262) snaps into the position shown in FIG. 18D, an audible click or snap may be heard or felt. As a result, the user receives audible and/or tactile confirmation that lock tooth (336) has moved from between one set of cam teeth (333, 335) to another or otherwise has rotated by a single articulation increment. When in the position shown in FIG. 18D, first cam member (330) stops rotating and lock tooth (236) fits between cam teeth (333, 335). Closure ring (236) and accordingly end effector (240) stop articulating. A positive lock has formed because any rotational motion of second cam member (331) urged by transverse forces on end effector (240) would result in parallel sides (386) engaging parallel sides (383) and stopping any further rotation of second cam member (331), which locks the articulation of end effector (240). It should be understood that the transition from the configuration shown in FIG. 18A to the configuration shown in FIG. 18D represents articulation through one articulation increment, or increment of articulation motion, in which the distance is defined generally by the spaces between second cam teeth (335).

It will be understood that in the position shown in FIG. 18D, end effector (240) has articulated thereby providing the user with a shaft assembly (200) with an articulated end effector (240). It will be appreciated that the user may wish to use shaft assembly (200) in the position shown in FIG. 18D or may wish to pivot end effector (240) further by one or more additional articulation increments. In the event that the user does not rotate articulation knob (235) further, the locking of lock tooth (336) between first cam teeth (333) and second cam teeth (335) prevents end effector (240) from pivoting to return to a straight position. Once end effector (240) has been articulated to a desired angle (a), it will be understood that the user may actuate firing beam (282) to drive knife member (280) to cut and drive staples (77) through tissue. For instance, knife member (280) and firing beam (282) may be in communication through, for instance, a bendable beam such that firing beam (282) can advance through any degree of pivot of articulation joint (234).

Figure 18E:
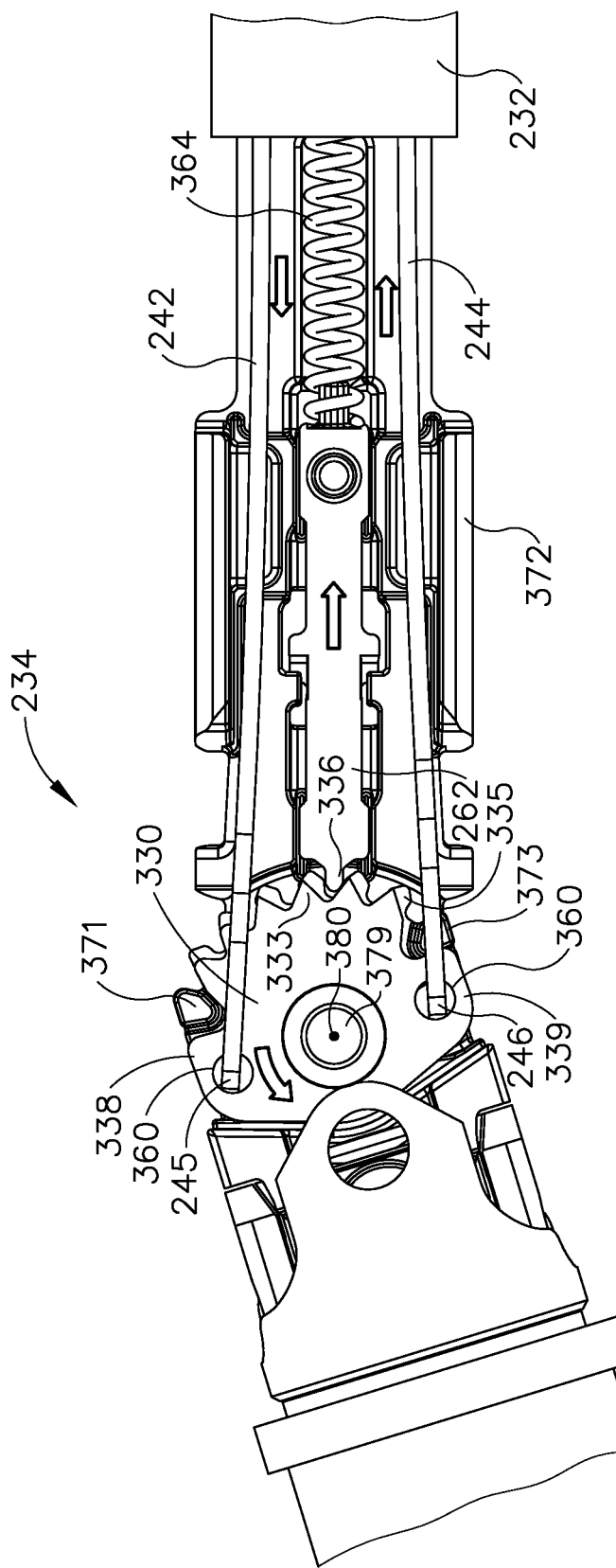
FIG. 18E depicts a top, partially internal view of the articulation joint of the shaft assembly of FIG. 13A with the first and second arms rotating the first cam member yet even further.
Figure 20:
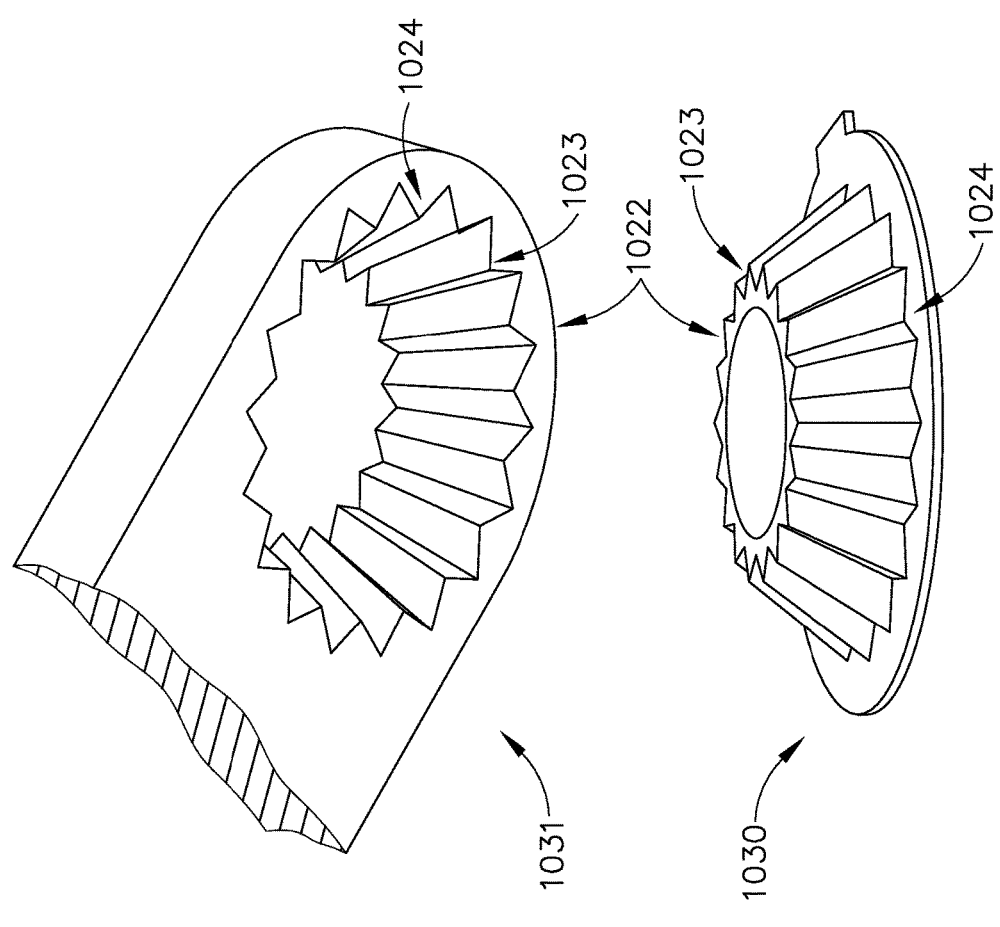
FIG. 20 depicts a perspective, exploded view of locking features of an exemplary alternative articulation joint.

FIG. 18E shows a fifth stage of actuation for articulation joint (234) in the event that the user wishes to pivot end effector (240) further. Once again, it will be understood that user continues to rotate articulation control knob (235). As a result, arms (242, 244) continue to move such that first arm (242) moves distally further and second arm (244) moves proximally further. Movement of arms (242, 244) continues to rotate first cam member (330), which causes cam wing (339) to push boss (373) rotationally. First cam member (330) and second cam member (331) move similarly as shown in FIGS. 18B-D, which causes end effector (240) to articulate further as well as lock in a more articulated position. It will be understood that the user may continue to rotate articulation control knob (235) to cause end effector (240) to pivot as far as the user desires. Furthermore, the user may rotate articulation control knob (235) in the opposite direction to cause arms (242, 244) and cam members (330, 331) to move in the opposite direction, thereby causing end effector (240) to articulate in an opposite direction.

As seen in the exemplary actuation shown in FIGS. 18A-18E, first cam member (330) is operable to unlock articulation joint (234) and pivot end effector (240) at articulation joint (234) about pivot axis (380), by transferring motion from arms (242, 244) to first cam member (330). In addition, second cam member (331) and lock bar (262) cooperate to lock articulation joint (234), to thereby lock the angle (a) of end effector (240) relative to the longitudinal axis (LA) of shaft assembly (200).

III. Exemplary Alternative Articulation Joints

In some instances, it may be desirable to provide alternative structures and methods for selectively locking and unlocking articulation joint (234). It may also be desirable to modify the structures and methods that are used to drive articulation joint (234) based on the alternative structures and methods that are used to selectively lock and unlock articulation joint (234). Various examples of alternative structures and methods that may be used to provide selective locking and unlocking of an articulation joint are described in greater detail below, while other examples will be apparent to those of ordinary skill in the art in view of the teachings herein. Similarly, various examples of alternative structures and methods that may be used to drive an articulation joint are described in greater detail below, while other examples will be apparent to those of ordinary skill in the art in view of the teachings herein. It should be understood that the following examples may be readily incorporated into articulation joint (234); or be readily eincorporated into shaft assembly (200) in place of articulation joint (234). Various suitable ways in which the following examples may be incorporated into instrument (10) will be apparent to those of ordinary skill in the art.

A. Exemplary Articulation Joint with Complementary Locking Members

FIGS. 20-22B show an exemplary alternative articulation joint (1034) which may be readily incorporated into shaft assembly (200). Articulation joint (1034) utilizes corresponding complementary locking members (1030, 1031) to lock and unlock articulation of end effector (240) at articulation joint (1034). In particular, FIG. 33 shows a first locking member (1030) and a second locking member (1031). As can be seen, locking members (1030, 1031) comprise a plurality of complementary interlocking features (1022). In the present example, each interlocking feature (1022) is generally shaped as a triangular protrusion (1023). Collectively, each interlocking feature (1022) is arranged around a generally conical internal diameter of each locking member (1030, 1031) to form a starburst pattern, with each protrusion (1023) forming an adjacent triangular trough (1024). In addition, each interlocking feature (1022) on first locking member (1030) is aligned to correspond to another interlocking feature (1022) on second locking member (1031) such that the first locking member (1030) and second locking member (1031) interlock with one another. In other words, for a given protrusion (1023) of first locking member (1030), there is a corresponding trough (1024) of second locking member (1031). Accordingly, when second locking member (1031) is inserted in first locking member (1030), first locking member (1030) and second locking member (1031) become interlocked such that they are rotationally fixed relative to each other. Second locking member (1031) is unitarily secured to end effector (240). Thus, when first locking member (1030) and second locking member (1031) are interlocked, the articulation position of end effector (240) is fixed.

Although locking members (1030, 1031) are shown as having triangular protrusions (1023), it should be understood that any other suitable geometry may be used. For instance, in other examples, a square, curved, or wavy geometry may be used. Additionally, although the present example is depicted as having a certain number of protrusions (1023), any suitable number of protrusions may be used. Of course, any other configuration suitable to lock relative rotation between locking members (1030, 1031) may be used as will be apparent to those of ordinary skill in the art in view of the teachings herein.

Figure 21:
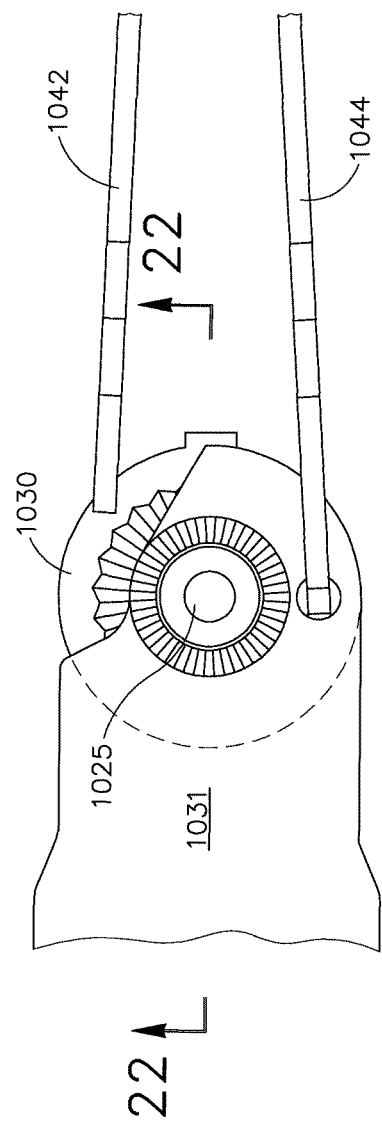
FIG. 21 depicts a top, plan view of the articulation joint incorporating the locking features of FIG. 20.

FIG. 21 shows a plan view of articulation joint (1034) with locking members (1030, 1031) are incorporated therein. As can be seen, articulation joint (1034) comprises a first arm (1042), a second arm (1043), a shaft (1025), and locking members (1030, 1031). Locking members (1030, 1031) are coaxially disposed about shaft (1025), which is oriented perpendicular to the longitudinal axis (LA) of shaft assembly (200). First locking member (1030) is keyed to shaft (1025) such that first locking member (1030) may translate along shaft (1025) but not rotate about shaft (1025). Second locking member (1031) is coupled with shaft such that second locking member (1031) can rotate about shaft (1025) but not translate along shaft (1025). Various ways in which these relationships may be provided will be apparent to those of ordinary skill in the art in view of the teachings herein. In the present example, second locking member (1031) is shown partially cut away so that the interaction between first arm (1042) and first locking member (1030) is visible. As will be described in greater detail below, first arm (1042) is operable to lock and unlock articulation of end effector (240) at articulation joint (1034) by disengaging (lock) or engaging (unlock) first locking member (1030). In contrast, second arm (1044) is secured to second locking member (1031) and is operable to articulate articulation joint (1034), as will be described in greater detail below. Thus, when articulation joint (1034) is unlocked, second locking member (1031) is operable to rotate about shaft (1025) thereby articulating end effector (240) relative to the longitudinal axis (LA) of shaft assembly (200).

Figure 22A:
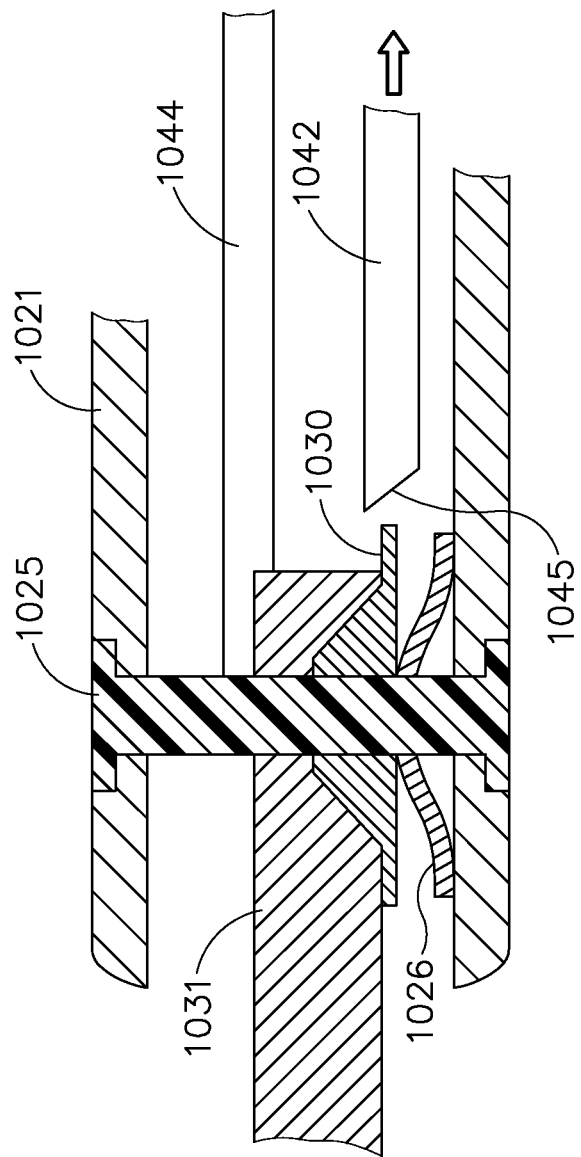
FIG. 22A depicts a side, cross-sectional view of the articulation joint of FIG. 20 taken along line 22-22 of FIG. 21, with a locking member in a locked position.
Figure 22B:
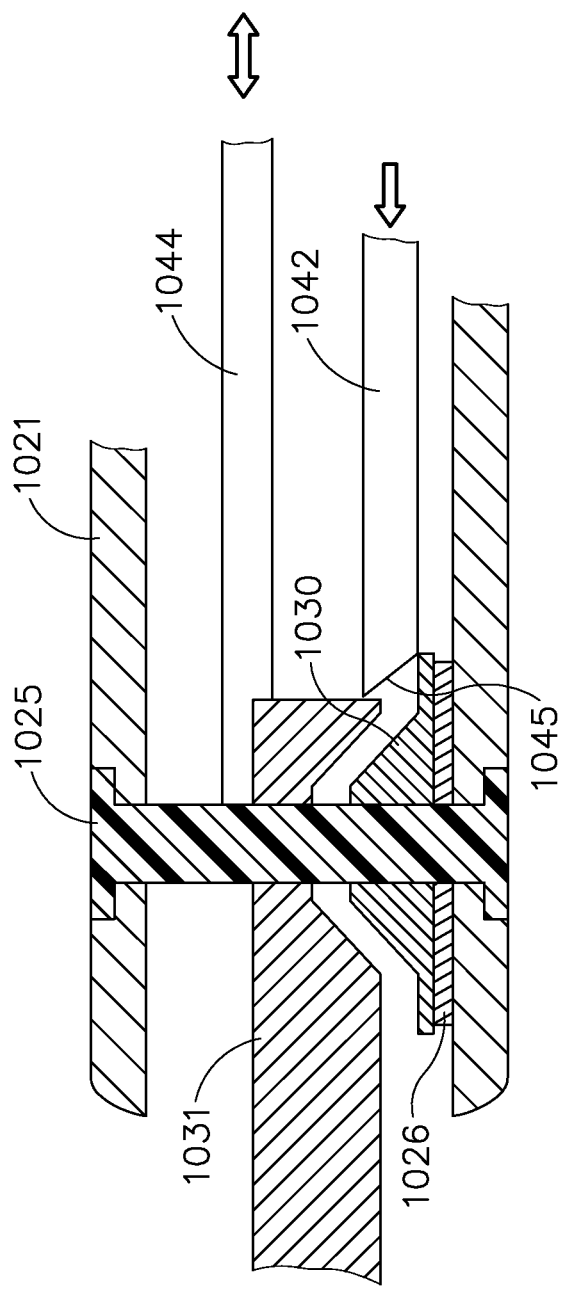
FIG. 22B depicts a side, cross-sectional view of the articulation joint of FIG. 20 taken along line 22-22 of FIG. 21, with the locking member in an unlocked position.

FIGS. 22A-B show cross-sectional views of exemplary operational states of articulation joint (1034). In particular, FIG. 22A shows articulation joint (1034) in a locked state. In the locked state, first locking member (1030) is urged into engagement with second locking member (1031) by a conical spring washer (1026) positioned around shaft (1025) and beneath first locking member (1030). As described above, first locking member (1030) is keyed to shaft (1025) such that first locking member (1030) can translate up and down relative to shaft (1025) but not rotate about shaft (1025). Accordingly, when first locking member (1030) is urged into engagement with second locking member (1031), first locking member (1030) prevents rotation of second locking member (1031) relative to shaft (1025) thereby locking articulation of articulation joint (1034). Shaft (1025) is shown as being fixed in place by a pair of retaining plates (1021).

FIG. 22B shows articulation joint (1034) in an unlocked state. In the unlocked state, first arm (1042) is actuated distally to engage first locking member (1030). First arm (1042) comprises an obliquely angled distal end (1045) that engages first locking member (1030), urging first locking member (1030) downwardly against the resilient bias provided by conical spring washer (1026). With first locking member (1030) urged downwardly, first locking member (1030) and second locking member (1031) become disengaged, thereby freeing second locking member (1031) to rotate about shaft (1025). With second locking member (1031) freely rotatable about shaft (1025), second arm (1044) may be actuated distally or proximally to articulate articulation joint (1034) counter clockwise or clockwise, respectively. Once a desired articulation angle is achieved, first arm (1042) may be retracted proximally. Conical spring washer (1026) returns first locking member (1030) to the upward position shown in FIG. 22A, thereby locking end effector (240) at the desired articulation angle at articulation joint (1034).

It should be understood that since first arm (1042) and second arm (1044) perform separate functions (e.g., locking/unlocking and rotating vs. only rotating), first arm (1042) and second arm (1044) may be actuated independently. As described above, this may include articulation control knob (35) being configured to actuate first arm (1042) and second arm (1044) independently. Alternatively, separate user input features may be provided to control arms (1042, 1044) separately, as described above.

B. Exemplary Articulation Joint with Helical Cam Member

Figure 23:
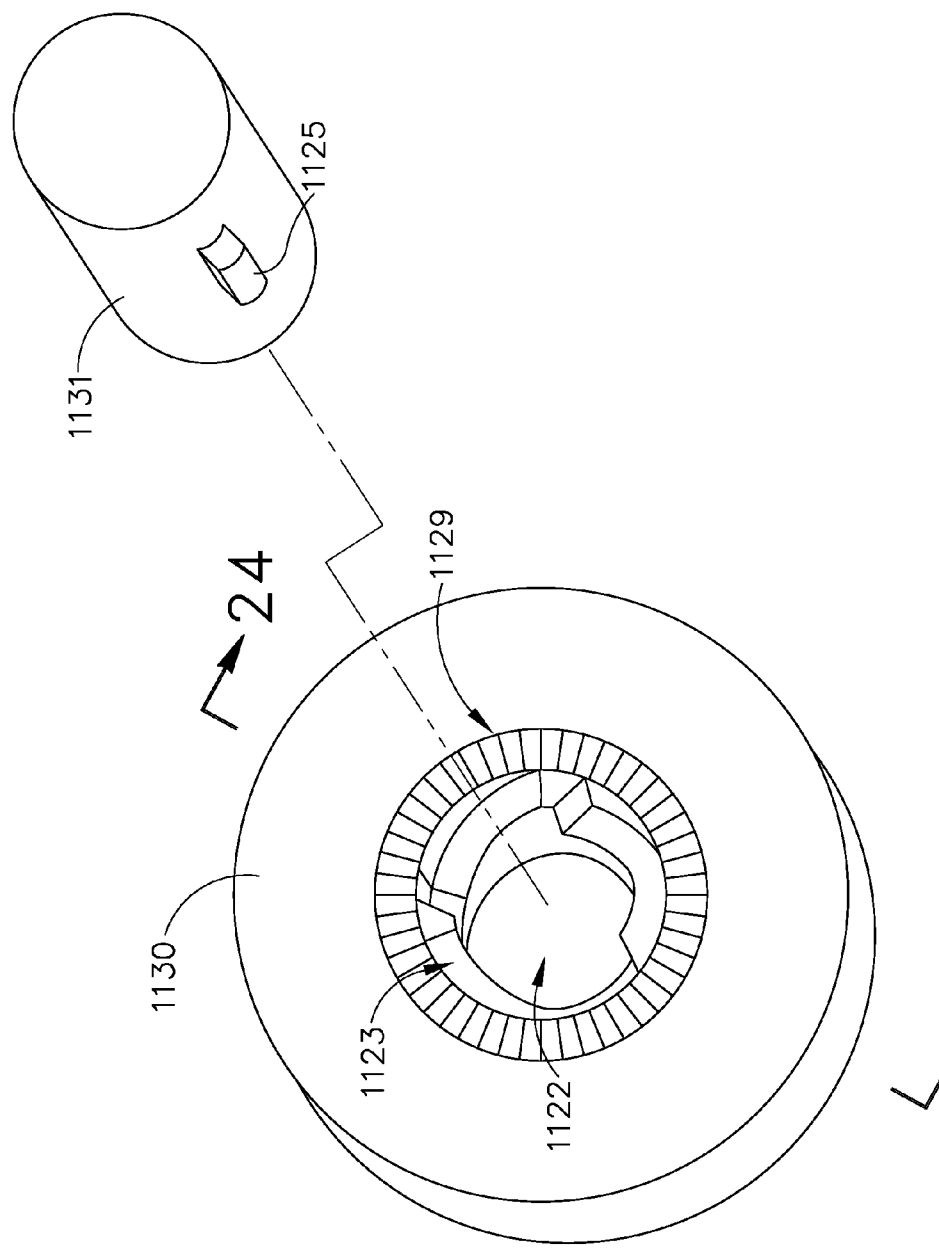
FIG. 23 depicts exploded view an exemplary alternative helical cam assembly.

FIGS. 23-25 show an exemplary alternative articulation joint (1134) which may be readily incorporated into shaft assembly (200). Articulation joint (1134) utilizes a helical cam member (1130) to lock and unlock articulation of end effector (240) at articulation joint (1134). As can be seen in FIG. 23, helical cam member (1130) is configured to receive a shaft (1131). As will be described in greater detail below, shaft (1131) is configured to translate about its longitudinal axis (but not rotate about its longitudinal axis) relative to helical cam member (1130) to lock and unlock articulation of end effector (240) at articulation joint (1134). Helical cam member (1130) is generally disk shaped, although helical cam member may be a variety of differing shapes. Helical cam member (1130) comprises a recessed hole (1122) through its center. On the underside of cam member (1130), a frustoconical, inwardly extending starburst locking feature (1129) is oriented around the outer edge of hole (1122). The inner diameter of hole (1122) has a plurality of helical camming features (1123). As can best be seen in FIG. 24, each helical camming feature (1123) comprises a ramped surface (1124) which permits a key (1125) of shaft (1131) to travel along ramped surface (1124). Inwardly extending locking feature (1129) is similar to second locking member (1031) described above and is likewise configured to engage with a complementary outwardly extending starburst locking feature (1128) of a locking member (1162), as will be described in greater detail below.

Shaft (1131) is generally cylindrical in shape and includes an integral key (1125) protruding radially outwardly from shaft (1131). The diameter of shaft generally corresponds to the inner diameter of hole (1122) of helical cam member (1130). Key (1125) is likewise sized to fit within each helical camming feature (1123) of helical cam member (1130). Thus, when shaft (1131) is inserted into hole (1122) of helical cam member (1130), key (1125) operable to travel along a particular helical camming feature (1123) of helical cam member (1130). Key (1125) may travel along helical camming feature (1123) of helical cam member (1130) as shaft (1131) is rotated relative to helical cam member (1130). Because helical camming feature (1123) is ramped, key (1125) is operable to translate shaft (1131) along the longitudinal axis of shaft (1131) as helical cam member (1130) is rotated about the longitudinal axis of shaft (1131). Similarly, when helical cam member (1130) is rotated in a clockwise For instance, when helical cam member (1130) is rotated in a counter clockwise motion, key (1025) will progressively travel up helical camming feature (1123) translating key (1125) out of opening (1122). motion, key (1125) will progressively travel down helical camming feature (1123) translating key (1125) along with shaft (1131) further inside of opening (1122). When key (1125) reaches the bottom of helical camming feature (1123) (e.g., when helical cam member (1130) is rotating with a counter clockwise motion), key (1125) may then travel along the exterior of helical cam member (1130) until it reaches the next helical camming feature (1123) where key (1125) may translate upwardly to the bottom of the next helical camming feature (1123). Likewise, when key (1125) reaches the top of helical camming feature (1123) (e.g., when shaft (1131) is rotating with a counter clockwise motion), key (1125) may prevent further clockwise rotation of helical cam member (1130).

FIG. 25A shows a cross-sectional view of articulation joint (1134). As can be seen, shaft (1131) is positioned between two retaining plates (1121) which hold shaft (1131) in position relative to shaft assembly (200). Retaining plates (1121) permit shaft (1131) to translate along the longitudinal axis of shaft (1131); yet prevent shaft (1131) from rotating about the longitudinal axis of shaft (1131). On the upper portion of the bottom retaining plate (1121), a conical spring washer (1126) (e.g., a Bellville washer) is positioned around shaft (1131). A locking member (1162) is positioned above spring washer (1126). At the proximal end of locking member (1162), the upper surface of locking member (1162) comprises outwardly presented locking feature (1128). Locking feature (1128) of locking member (1162) has a starburst configuration that complements the starburst configuration of locking feature (1129) of helical cam member (1130). Although not shown in FIG. 25A, the distal end of locking member (1162) is connected to end effector (240). Accordingly, locking member (1162) may articulate end effector (240) by pivoting about the longitudinal axis of shaft (1131). In some versions, locking member (1162) is configured to translate relative to end effector (240) along the longitudinal axis of shaft (1131), yet end effector (240) still rotates unitarily with locking member (1162) about the longitudinal axis of shaft (1131). Various suitable relationships that may be provided between locking member (1162) and end effector (240) will be apparent to those of ordinary skill in the art in view of the teachings herein.

Spring washer (1126) resiliently biases locking member (1162) upwardly so that locking feature (1128) engages the complementary locking feature (1129) of helical cam member (1130). Thus, in the configuration shown in FIG. 25A, locking member (1162) is in a locked position such that locking member (1162) and end effector (240) cannot rotate relative to helical cam member (1130). Helical cam member (1130) is vertically secured in position along the longitudinal axis of shaft (1131) such that helical cam member (1130) may rotate about the longitudinal axis of shaft (1131) yet helical cam member cannot translate along the longitudinal axis of shaft (1131). Various suitable ways in which helical cam member (1130) may be secured will be apparent to those of ordinary skill in the art in view of the teachings herein. In the present example, articulation joint (1134) includes bushings (1127) on each surface which contacts shaft (1131). Bushings (1127) may be configured to reduce friction and increase the durability of each respective surface. Of course, bushings (1127) are entirely optional and may be omitted in some examples.

As can be seen by comparing FIGS. 25A and 25B, locking member (1162) may be unlocked and thereby permitted to rotate about shaft (1131) by rotating helical cam member (1130). In particular, FIG. 25A shows a first arm (1142) in phantom. The first arm (1142) may be attached to helical cam member (1130) and may be used to rotate helical cam member (1130) about shaft (1131), between the positions shown in FIGS. 25A and 25B. As can be seen in FIG. 25B, when helical cam member (1130) is rotated from the position shown in FIG. 25A to the position shown in FIG. 25B, key (1125) of shaft (1131) is driven downwardly by helical camming feature (1123) of helical cam member (1130). Key (1125) correspondingly drives locking member (1162) downwardly, such that locking feature (1128) of a locking member (1162) disengages locking feature (1129) of helical cam member (1130). With locking member (1162) out of engagement with helical cam member (1130), locking member (1162) may be rotated about to shaft (1131) via a second arm (1144) attached thereto (shown in phantom in FIG. 25A), to thereby articulate end effector (240).

Once locking member (1162) is rotated to a desired position, articulation joint (1134) may be relocked by returning articulation joint (1134) to the position shown in FIG. 25A. In particular, helical cam member (1130) may be rotationally advanced or retracted via first arm (1142). For instance, if helical cam member (1130) is rotationally advanced, key (1125) may engage the next helical camming feature (1123), thus shifting to the top of the next helical camming feature (1123). Similarly, if helical cam member (1130) is rotationally retracted, key (1125) may slide up the ramped surface of the same helical camming feature (1123) used to advance key (1125) outwardly. Although helical cam member (1130) is shown as being used with conical starburst locking features (1128, 1129), it should be understood that helical cam member (1130) may be used with any suitable locking system utilizing a translating shaft as will be apparent to those of ordinary skill in the art in view of the teachings herein.

C. Exemplary Articulation Joint with Pivoting Locking Member

Figure 26:
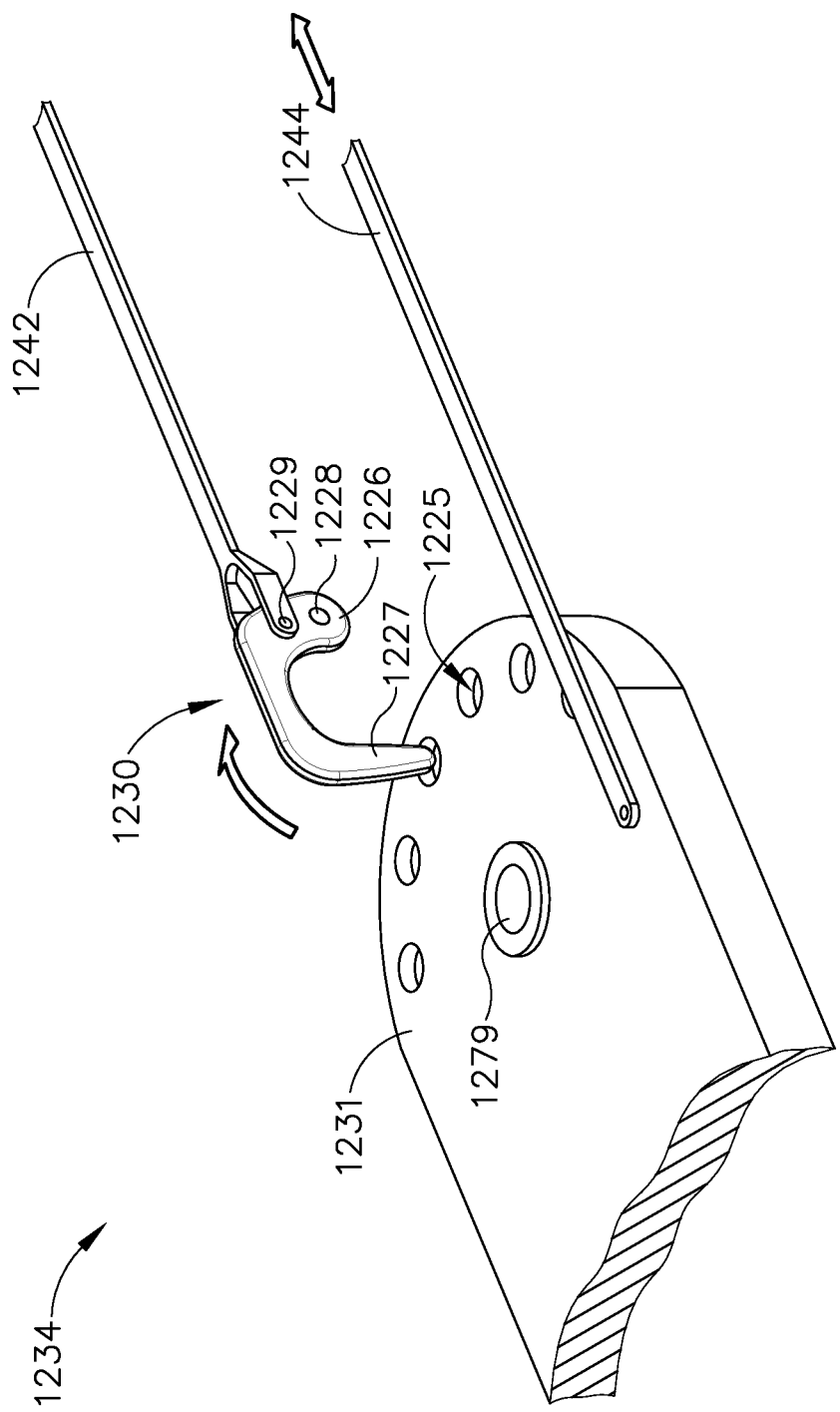
FIG. 26 depicts a perspective view of an exemplary alternative articulation joint.

FIG. 26 depicts an exemplary alternative articulation joint (1234) for use with shaft assembly (200) that utilizes a pivoting lock member (1230) to lock and unlock a single lock member (1231). In particular, articulation joint (1234) comprises lock member (1231), pivoting lock member (1230), a first arm (1242), and a second arm (1244). Lock member (1231) comprises a plurality of holes (1225) which may be used to lock articulation joint (1234) in a plurality of discrete articulation positions, with each articulation position having a specific angle (a) relative to the longitudinal axis (LA) of shaft assembly (200). Similar to articulation joint (234), articulation joint (1234) is rotatable about a central shaft (1279) to achieve articulation. Central shaft (1279) extends along an axis that is perpendicular to the longitudinal axis (LA) of shaft assembly (200). Although not shown in FIG. 26, it should be understood that the distal end of lock member (1231) may be unitarily attached to end effector (240). Thus, rotation of lock member (1231) about central shaft (1279) causes end effector (240) to articulate about the longitudinal axis of central shaft (1279) at articulation joint (1234).

Lock member (1230) is generally L-shaped with a pivot portion (1226) and a locking portion (1227). Pivot portion (1226) is configured to pivot about a pivot shaft (1228) to pivot locking portion (1227) into and out of engagement with lock member (1231) thereby locking and unlocking lock member (1231), respectively. Locking portion (1227) is configured to fit within each hole (1225) of lock member (1231). Pivot shaft (1228) is oriented along an axis that is substantially perpendicular the longitudinal axis of central shaft (1279). The axis of pivot shaft (1228) is also perpendicular to the longitudinal axis (LA) of shaft assembly (200).

In an exemplary mode of operation, articulation joint (1234) is operable to articulate using independently actuated first arm (1242) and second arm (1244). For instance, first arm (1242) is shown as being pivotally attached to pivot portion (1226) of lock member (1230) via a pin (1229).

Accordingly, first arm (1242) may be actuated distally to pivot locking portion (1227) of lock member (1230) into a hole (1225) of lock member (1230), thereby locking articulation joint (1234). Likewise, first arm (1242) may also be actuated proximally to pivot locking portion (1227) of lock member (1230) out of a hole (1225) of lock member (1230) thereby unlocking articulation joint (1234). When articulation joint (1234) is unlocked, second arm (1244), which is attached to lock member (1231), may be actuated to rotate lock member (1231) about central shaft (1279) thereby articulating articulation joint (1234). Second arm (1244) may be actuated proximally or distally depending upon whether a clock wise or counter clockwise articulation is desired. Once a desired articulation position is reached, end effector (240) may be relocked at the desired articulation position at articulation joint (1234) by pivoting lock member (1230) into engagement with a new hole (1225) via distal advancement of first arm (1242).

D. Exemplary Articulation Joint with Translating Locking Member

Figure 27:
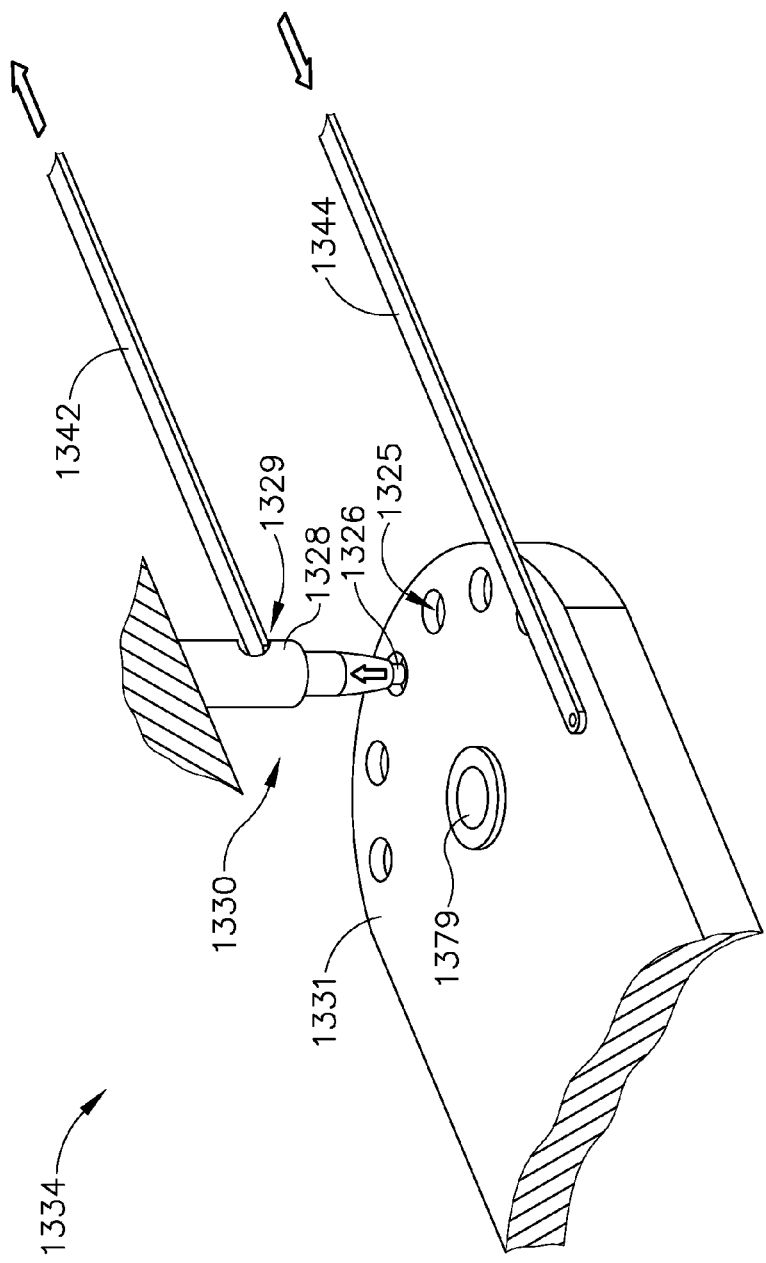
FIG. 27 depicts a perspective view of another exemplary alternative articulation joint.
Figure 28:
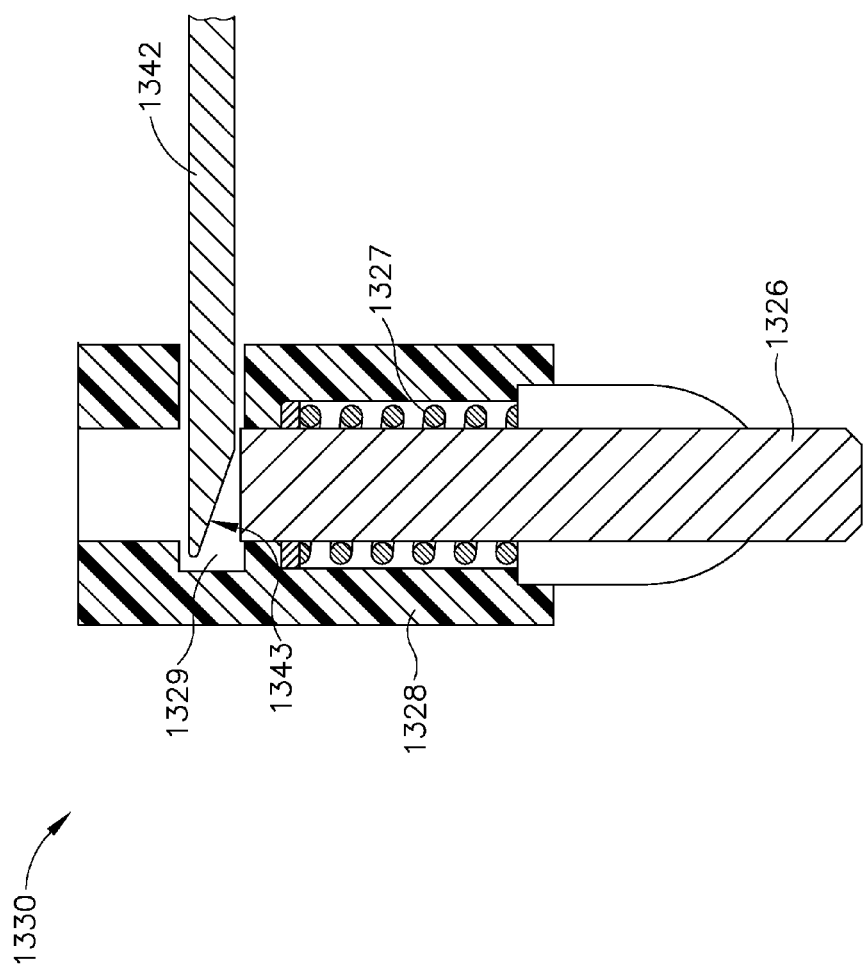
FIG. 28 depicts a cross-sectional side view of an actuation assembly of the articulation joint depicted in FIG. 27.

FIGS. 27-28 depict an exemplary alternative articulation joint (1334) for use with shaft assembly (200) that utilizes a translating lock member (1330) to lock and unlock a single lock member (1331). In particular, articulation joint (1334) comprises lock member (1331), translating lock member (1330), a first arm (1342), and a second arm (1344). Lock member (1331) comprises a plurality of holes (1325) which may be used to lock articulation joint (1334) in a plurality of discrete articulation positions, with each articulation position having a specific angle (a) relative to the longitudinal axis (LA) of shaft assembly (200). Similar to articulation joint (234), articulation joint (1334) is rotatable about a central shaft (1379) to achieve articulation. Central shaft (1379) extends along an axis that is perpendicular to the longitudinal axis (LA) of shaft assembly (200). Although not shown in FIG. 27, it should be understood that the distal end of lock member (1331) may be unitarily attached to end effector (240). Thus, rotation of lock member (1331) about central shaft (1379) causes end effector (240) to articulate about the longitudinal axis of central shaft (1379) at articulation joint (1334).

FIG. 28 shows a cross-sectional view of lock member (1330). As can be seen, lock member (1330) comprises a translatable locking feature (1326), a spring (1327), and a casing (1328). Locking feature (1326) is generally cylindrical in shape such that locking feature (1326) may translate along an axis that is both perpendicular to the longitudinal axis (LA) of shaft assembly (200) and parallel to the longitudinal axis of central shaft (1379). In particular, locking feature (1326) is operable to translate into and out of a hole (1325) of lock member (1331). Locking feature (1326) is resiliently biased upwardly by spring (1327). Although spring (1327) is shown as resiliently biasing locking feature (1326), it should be understood that any suitable means may be used to resiliently bias locking feature (1326) upwardly. Casing (1328) is configured to surround locking feature (1326) such that locking feature (1326) may slidably engage with casing (1328). Casing (1328) is shown as having a transverse bore (1329) which, as will be described in greater detail below, permits first arm (1342) to translate into and out of casing (1328) so that an obliquely angled distal end (1343) of first arm (1342) may actuate locking feature (1326).

In an exemplary mode of operation, articulation joint (1334) is operable to articulate using independently actuated first arm (1342) and second arm (1344). For instance, first arm (1242) is shown as being translatable into and out of casing (1328) of lock member (1330). In particular, as can be seen in FIG. 41, oblique distal end (1343) of first arm (1342) is operable to drive locking feature (1326) of lock member (1330) downwardly through a camming action when first arm (1342) is actuated distally. Thus, distal actuation of first arm (1342) is operable to translate locking feature (1326) downwardly into a hole (1325) of lock member (1321) to lock articulation joint (1334). Likewise, first arm (1342) may also be actuated proximally to disengage locking feature (1326) of lock member (1330) to permit spring to resiliently drive locking feature (1326) upwardly and out of engagement with a hole (1325) of lock member (1330). Thus, proximal actuation of first arm (1342) will unlock articulation joint (1334). When articulation joint (1334) is unlocked, second arm (1344), which is attached to lock member (1331), may be actuated to rotate lock member (1331) about central shaft (1379) thereby articulating articulation joint (1334). Second arm (1344) may be actuated proximally or distally depending upon whether a clock wise or counter clockwise articulation is desired. Once a desired articulation position is reached, end effector (240) may be relocked at the desired articulation position at articulation joint (1334) by actuating locking feature (1326) into engagement with a new hole (1325) via distal advancement of first arm (1342).

IV. Miscellaneous

It should be understood that in the various examples described above, an articulation joint is configured to permit an end effector to articulate along a first plane and thereby deflect away from the longitudinal axis of a shaft assembly. A locking assembly is operable to selectively lock the articulation joint. The locking assembly includes a locking member that is movable along a second plane to selectively engage the first locking member and thereby lock the articulation joint. The second plane is offset from the first plane. The second plane is also non-parallel with the first plane. In some instances, the second locking member is movable along a second axis that is perpendicular to the longitudinal axis of the shaft assembly. An unlocking member may selectively drive the locking member. The unlocking member may move along a third plane, which may be offset from and/or in a non-parallel relationship with the first and/or second plane(s). The unlocking member may move along a third axis, which may be perpendicular to the longitudinal axis of the shaft assembly and/or the second axis.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims. It should also be understood that the various teachings herein may be readily combined with the teachings of the various references that are cited herein. In addition, the various teachings herein may be readily combined with the teachings of U.S. Pub. No. 2015/0374362, entitled "Method of Unlocking Articulation Joint in Surgical Stapler," published Dec. 31, 2015, the disclosure of which is incorporated by reference herein; and/or the teachings of U.S. Pub. No. 2015/0374364, published Dec. 31, 2015, entitled "Translatable Articulation Joint Unlocking Feature for Surgical Stapler," now U.S. Pat. No. 9,693,774, issued Jul. 4, 2017, the disclosure of which is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning, " issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, now U.S. Pat. No. 8,844,789, issued Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, now U.S. Pat. No. 8,820,605, issued Sep. 2, 2014, the disclosure of which is incorporated by reference herein; U.S. Pub. No. 2012/0132450, entitled "Shiftable Drive Interface for Robotically-Controlled Surgical Tool," published May 31, 2012, now U.S. Pat. No. 8,616,431, issued Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, now U.S. Pat. No. 8,573,461, issued Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, now U.S. Pat. No. 8,602,288, issued Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No. 9,301,759, issued Apr. 5, 2016, the disclosure of which is incorporated by reference herein; U.S. Pub. No. 2012/0203247, entitled "Robotically-Controlled Surgical End Effector System," published Aug. 9, 2012, now U.S. Pat. No. 8,783,541, issued Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012; now U.S. Pat. No. 8,479,969, issued Jul. 9, 2013; U.S. Pub. No. 2012/0138660, entitled "Robotically-Controlled Cable-Based Surgical End Effectors," published Jun. 7, 2012, now U.S. Pat. No. 8,800,838, issued Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, now U.S. Pat. No. 8,573,465, issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body;
   (b) a shaft assembly extending distally from the body, wherein the shaft assembly defines a longitudinal axis, wherein the shaft assembly has a distal end;
   (c) an end effector, wherein the end effector is operable to manipulate tissue;
   (d) an articulation joint coupling the end effector with the distal end of the shaft assembly, wherein the articulation joint is configured to permit the end effector to articulate along a first plane and thereby deflect away from the longitudinal axis of the shaft assembly; and
   (e) a locking assembly operable to selectively lock the angular position of the end effector relative to the longitudinal axis of the shaft assembly, wherein the locking assembly comprises:
      (i) a first locking member unitarily secured to the end effector, such that the first locking member is configured to move with the end effector relative to the longitudinal axis of the shaft assembly, and
      (ii) a second locking member operable to selectively engage the first locking member to thereby selectively lock the angular position of the end effector relative to the longitudinal axis of the shaft assembly, wherein the second locking member is movable along a second plane to selectively engage the first locking member, wherein the second plane is offset from the first plane, and wherein the second plane is non-parallel with the first plane;
   wherein the locking assembly further comprises an unlocking feature, wherein the unlocking feature is operable to selectively disengage the second locking member from the first locking member; and
   wherein the second locking member is movable along a first axis, wherein the unlocking feature is operable to translate along a second axis to thereby selectively disengage the second locking member from the first locking member, wherein the second axis is perpendicular to the first axis.

2. The apparatus of claim 1, wherein the second axis is parallel with the longitudinal axis of the shaft assembly.

3. The apparatus of claim 1, wherein the unlocking feature includes a distal end having a camming feature, wherein the camming feature is operable to drive the second locking member along the second axis in response to translation of the unlocking feature along the second axis.

4. The apparatus of claim 1, wherein the unlocking feature is operable to rotate about a first axis to thereby selectively disengage the second locking member from the first locking member.

5. The apparatus of claim 4, wherein the second locking member is movable along a second axis, wherein the first axis and the second axis are coextensive with each other.

6. The apparatus of claim 5, wherein the second locking member and the unlocking feature are both coaxially disposed about the first and second axes.

7. The apparatus of claim 4, wherein the unlocking feature comprises a helical cam feature operable to bear against the second locking member.

8. The apparatus of claim 7, wherein the second locking member comprises an outwardly extending key configured to engage the helical cam of the unlocking feature.

9. The apparatus of claim 1, wherein the second locking feature is resiliently biased to engage the first locking feature.

10. The apparatus of claim 1, wherein the articulation joint is configured to permit the end effector to pivot about a first axis to thereby permit the end effector to deflect away from the longitudinal axis of the shaft assembly.

11. The apparatus of claim 10, wherein the second locking member is movable along a second axis, wherein the first axis and the second axis are coextensive with each other.

12. The apparatus of claim 1, wherein the first and second locking members comprise complementary starburst features.

13. The apparatus of claim 1, wherein the shaft assembly further comprises:
   (i) a first translatable member, wherein the first translatable member is operable to selectively drive the second locking member, and
   (ii) a second translatable member, wherein the second translatable member is operable to selectively drive the end effector to deflect the end effector from the longitudinal axis of the shaft assembly at the articulation joint.

14. The apparatus of claim 1, wherein the first locking member defines a plurality of openings, each opening being associated with a different angular position of the end effector relative to the longitudinal axis of the shaft assembly, wherein each opening is configured to selectively receive a portion of the second locking member to thereby selectively lock the angular position of the end effector relative to the longitudinal axis of the shaft assembly.

15. The apparatus of claim 1, wherein the end effector comprises a stapling assembly operable to drive staples into tissue.

16. An apparatus comprising:
   (a) a body;
   (b) a shaft assembly extending distally from the body, wherein the shaft assembly defines a longitudinal axis, wherein the shaft assembly has a distal end;
   (c) an end effector, wherein the end effector is operable to manipulate tissue;
   (d) an articulation joint coupling the end effector with the distal end of the shaft assembly, wherein the articulation joint is configured to permit the end effector to pivot about a pivot axis to thereby pivot away from the longitudinal axis of the shaft assembly; and
   (e) a locking assembly operable to selectively lock the angular position of the end effector relative to the longitudinal axis of the shaft assembly, wherein the locking assembly comprises:
      (i) a first locking member unitarily secured to the end effector proximal to the pivot axis, such that the first locking member is configured to pivot with the end effector about the pivot axis,
      (ii) a second locking member operable to selectively engage the first locking member to thereby selectively lock the angular position of the end effector relative to the longitudinal axis of the shaft assembly, wherein the second locking member is movable along the pivot axis to selectively engage the first locking member; and (iii) an unlocking feature operable to selectively disengage the second locking member from the first locking member, wherein the unlocking feature is operable to translate along an axis that is perpendicular to the pivot axis to thereby selectively disengage the second locking member from the first locking member.

17. An apparatus comprising:
(a) a body;
(b) a shaft assembly extending distally from the body, wherein the shaft assembly defines a longitudinal axis, wherein the shaft assembly has a distal end;
(c) an end effector, wherein the end effector is operable to manipulate tissue;
(d) an articulation joint coupling the end effector with the distal end of the shaft assembly, wherein the articulation joint is configured to permit the end effector to articulate along a first plane and thereby deflect away from the longitudinal axis of the shaft assembly; and
(e) a locking assembly operable to selectively lock the angular position of the end effector relative to the longitudinal axis of the shaft assembly, wherein the locking assembly comprises:
(i) a first locking member unitarily secured to the end effector, such that the first locking member is configured to move with the end effector relative to the longitudinal axis of the shaft assembly, and
(ii) a second locking member operable to selectively engage the first locking member to thereby selectively lock the angular position of the end effector relative to the longitudinal axis of the shaft assembly, wherein the second locking member is movable along a second plane to selectively engage the first locking member, wherein the second plane is offset from the first plane, and wherein the second plane is non-parallel with the first plane;

wherein the locking assembly further comprises an unlocking feature operable to selectively disengage the second locking member from the first locking member, wherein the second locking member is movable along a first axis; and wherein the unlocking feature is operable to translate along a second axis to thereby selectively disengage the second locking member from the first locking member, wherein the second axis is perpendicular to the first axis, wherein the unlocking feature includes a distal end having a camming feature, wherein the camming feature is operable to drive the second locking member along the second axis in response to translation of the unlocking feature along the second axis.

18. The apparatus of claim 17, wherein the second axis is parallel with the longitudinal axis of the shaft assembly.

* * * * *